US012577549B2

(12) United States Patent
Yang et al.

(10) Patent No.: US 12,577,549 B2
(45) Date of Patent: Mar. 17, 2026

(54) MODIFIED POLYPEPTIDE HAVING XYLANASE ACTIVITY

(71) Applicant: KEMIN INDUSTRIES, INC., Des Moines, IA (US)

(72) Inventors: Tae Joo Yang, Seoul (KR); Jihyun Shim, Seoul (KR); Eun Jung Choi, Seoul (KR); Byung-sam Son, Seoul (KR); Jae Yong Park, Seoul (KR)

(73) Assignee: KEMIN INDUSTRIES, INC., Des Moines, IA (US)

( * ) Notice: Subject to any disclaimer, the term of this patent is extended or adjusted under 35 U.S.C. 154(b) by 363 days.

(21) Appl. No.: 18/267,531

(22) PCT Filed: Dec. 15, 2021

(86) PCT No.: PCT/KR2021/019114
§ 371 (c)(1),
(2) Date: Jun. 15, 2023

(87) PCT Pub. No.: WO2022/131799
PCT Pub. Date: Jun. 23, 2022

(65) Prior Publication Data
US 2024/0110170 A1      Apr. 4, 2024

(30) Foreign Application Priority Data
Dec. 15, 2020      (KR) ........................ 10-2020-0175801

(51) Int. Cl.
*C12N 9/24*      (2006.01)

(52) U.S. Cl.
CPC .... *C12N 9/2482* (2013.01); *C12Y 302/01008* (2013.01)

(58) Field of Classification Search
CPC .......... C12N 9/2482; C12Y 302/01008; A21D 8/042; A23L 7/107; A23L 7/104; A23L 29/06; Y02E 50/10; C12P 19/00; C12P 19/02; C12P 19/14; D21C 9/10; C10L 1/10
See application file for complete search history.

(56) References Cited

U.S. PATENT DOCUMENTS

| | | | |
|---|---|---|---|
| 7,615,362 B2 | 11/2009 | Cheng et al. | |
| 7,749,743 B2* | 7/2010 | Chen ................... | C12N 9/2485 435/200 |
| 2008/0118491 A1 | 5/2008 | Cheng et al. | |
| 2008/0254539 A1 | 10/2008 | Chen et al. | |
| 2009/0148923 A1 | 6/2009 | Sung | |

FOREIGN PATENT DOCUMENTS

| | | |
|---|---|---|
| JP | 2003-511066 A | 3/2003 |
| KR | 10-2013-0025770 A | 3/2013 |
| KR | 10-2019-0069014 A | 6/2019 |
| WO | 2016/072448 A1 | 5/2016 |
| WO | 2023/075496 A1 | 5/2023 |

OTHER PUBLICATIONS

Banerjee et al., Improving enzymes for biomass conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Beg et al., "Microbial xylanases and their industrial applications: a review," Appl Microbiol Biotechnol, 56: 326-338 (2001).
International Search Report issued in corresponding International Patent Application No. PCT/KR2021/019114 dated Apr. 11, 2022.
Molecular Cloning A Laboratory Manual, Third Edition, ed by Sambrook and Russell, Cold Spring Harbor Laboratory Press, vol. 2, 2001, 5 pages.
Trevizano et al., "Thermostability improvement of *Orpinomyces* sp. *xylanase* by directed evolution", Journal of Molecular Catalysis B: Enzymatic, vol. 81, 2012, pp. 12-18.
Orpinomyces xylanase (XYNE1) enzyme, SEQ: 1., BAS62101, Mar. 27, 2013, 1 page, XP002811683.
Database UniProt, RecName: Full=Endo-1, 4-beta-xylanase {ECO:0000256IARBA:ARBA00012590, ECO:0000256IPROSITE-ProRule:PRU01097},                                    EC=3.2.1.8 {ECO:0000256:ARBA:ARBA00012590, ECO:0000256IPROSITE-ProRule:PRU01097}, Database accession No. A0A371AUB0, Nov. 7, 2018, 1 page, XP002811693.
Database UniProt, RecName: Full=Beta-xylanase {ECO:0000256iRuleBase:RU361174}; EC=3 .2 .1. 8 {ECO:00002561RuleBase:RU361174}, Database accession No. AOA354K6U4, Nov. 7, 2018, 2 pages, XP002811694.

(Continued)

*Primary Examiner* — Ganapathirama Raghu
(74) *Attorney, Agent, or Firm* — Nyemaster Goode P.C.

(57) ABSTRACT

The present disclosure relates to a modified polypeptide having xylanase activity and the use thereof.

11 Claims, 5 Drawing Sheets

Specification includes a Sequence Listing.

(56)                    References Cited

OTHER PUBLICATIONS

Extended European Search Report issued in corresponding European Patent Application No. 21907103.2, dated Jun. 26, 2024.
Office Action issued in corresponding Japanese Patent Application No. 2023-536401, dated Jun. 20, 2024 with an English translation.

* cited by examiner

[FIG. 1]
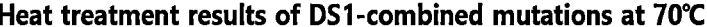
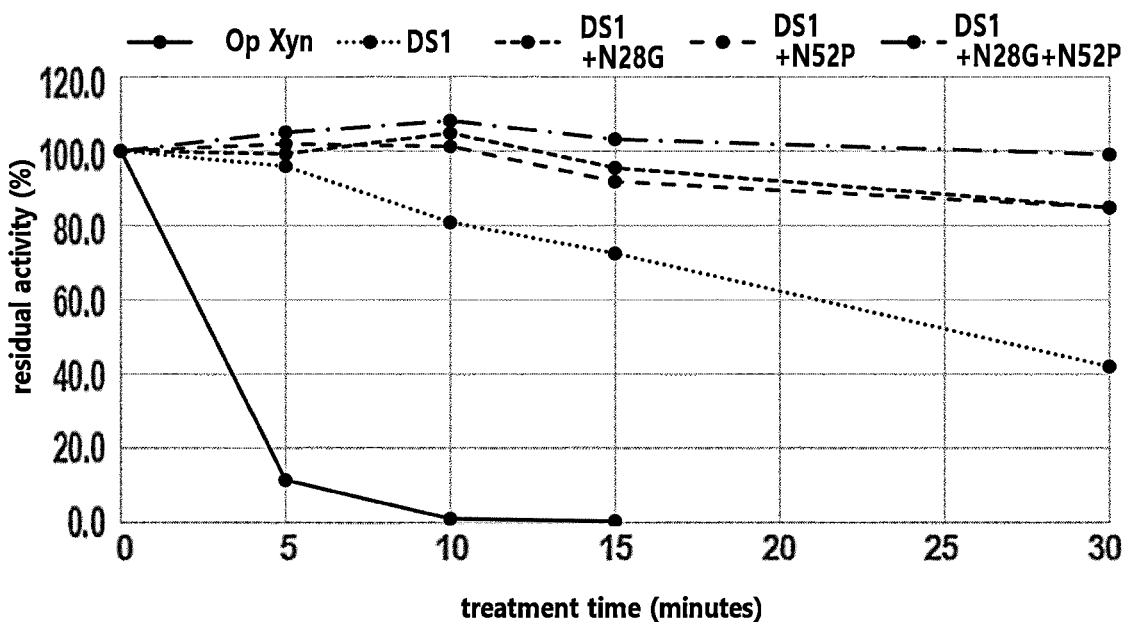

[FIG. 2]
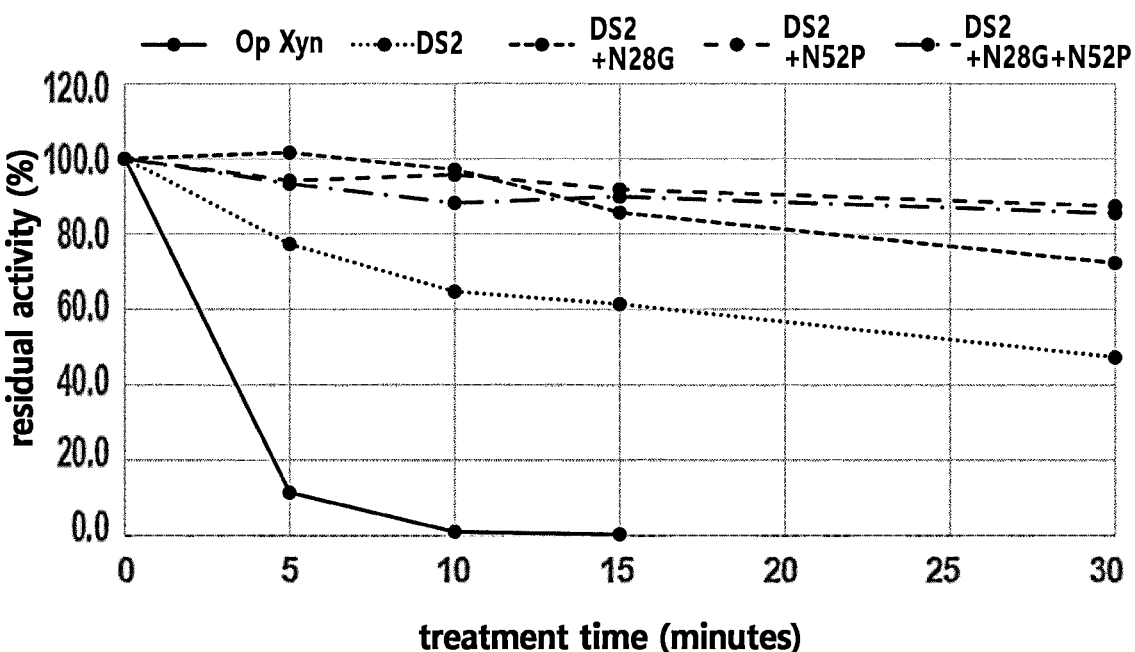
Heat treatment results of DS2-combined mutations at 70°C

[FIG. 3]
Heat treatment results of DS5-combined mutations at 70℃
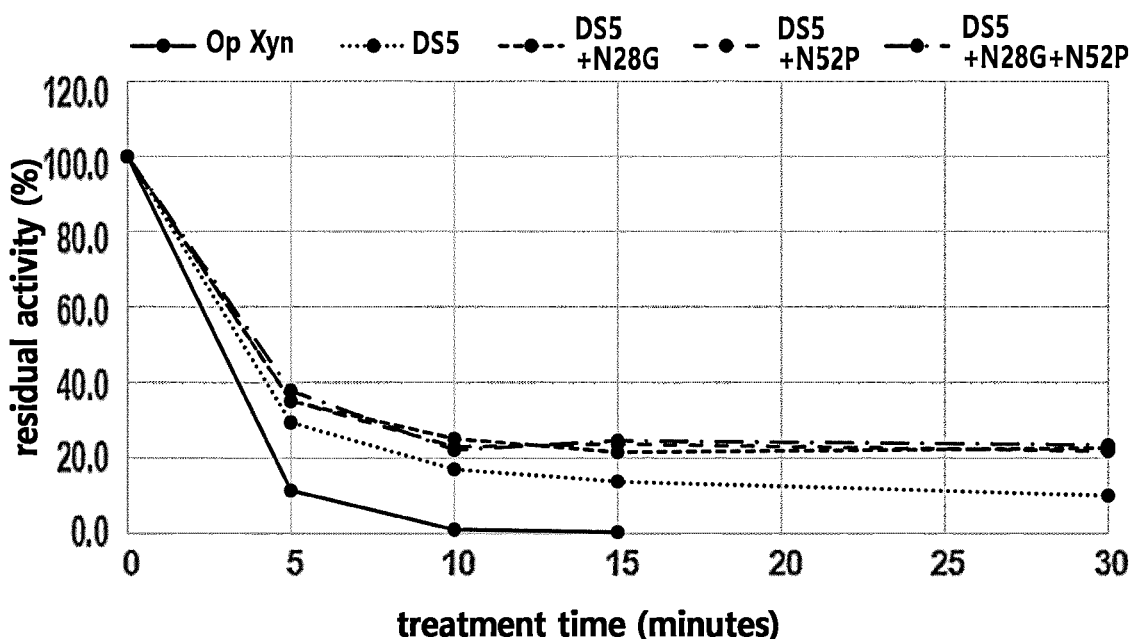

[FIG. 4]
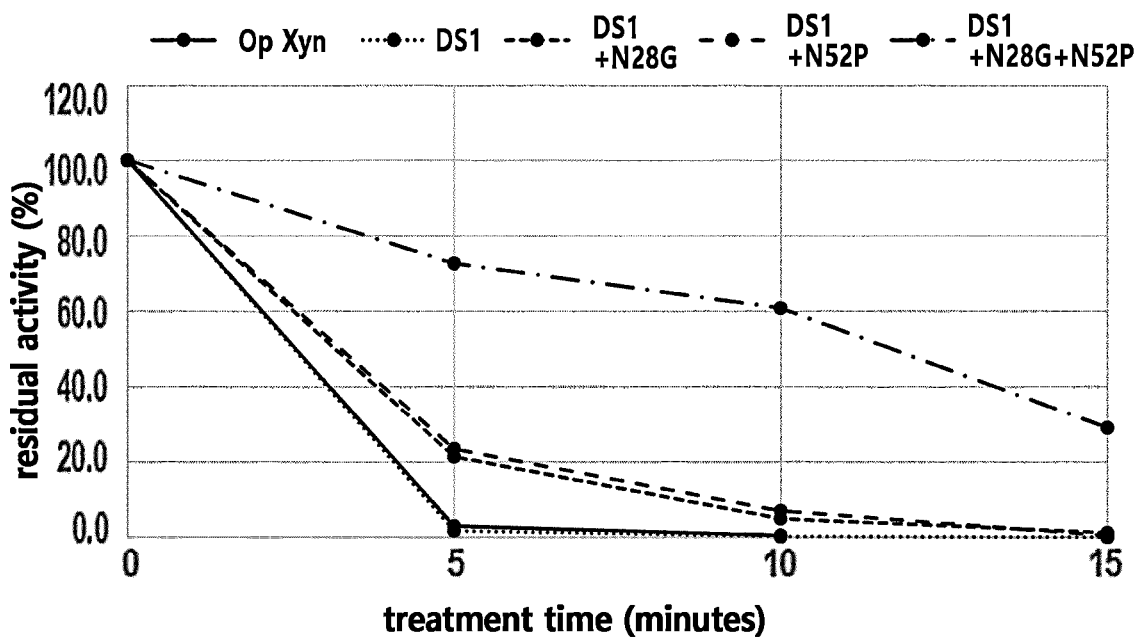
Heat treatment results of DS1-combined mutations at 80°C

[FIG. 5]
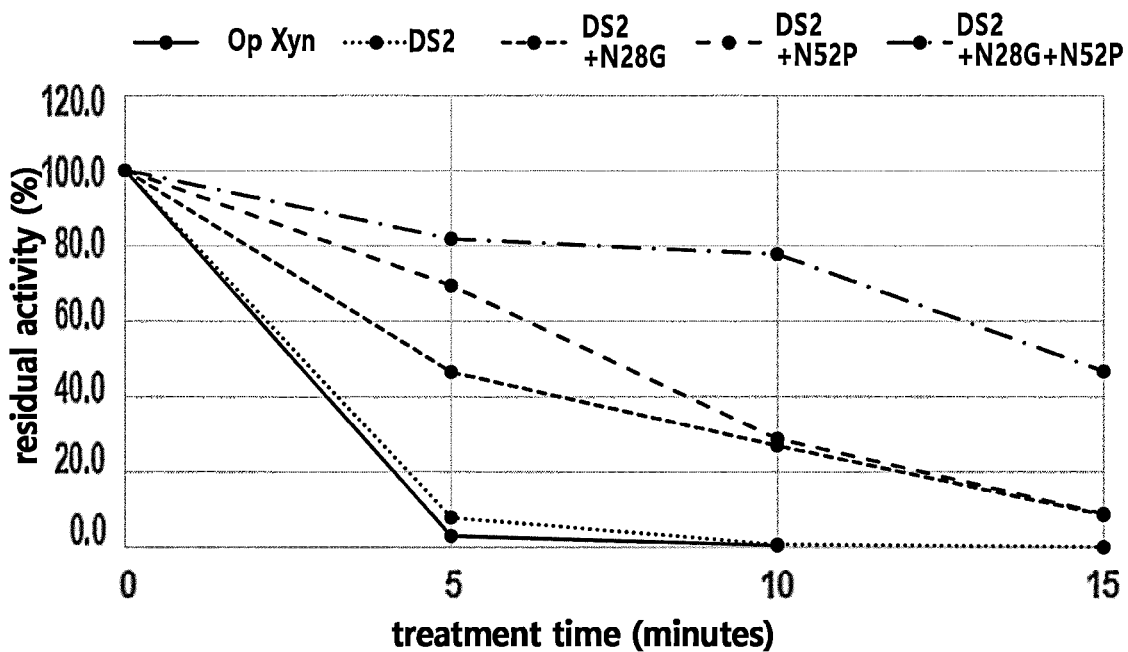

MODIFIED POLYPEPTIDE HAVING XYLANASE ACTIVITY

A computer readable text file, entitled "105135-5068-US_Sequence_Listing.txt," created on or about Jun. 26, 2023, with a file size of 50,519 bytes contains the sequence listing for this application and is hereby incorporated by reference in its entirety.

TECHNICAL FIELD

The present disclosure relates to a modified polypeptide having xylanase activity and the use thereof

BACKGROUND ART

Xylanase (EC 3.2.1.8) is a hydrolase that randomly degrades the β-1,4 backbone of xylan, a component of plant cell walls. Xylanase is mainly used to break down biomass in areas such as animal feed, baking, pulp bleaching, etc. (Beg Q K, Kapoor M, Mahajan L, Hoondal G S. Microbial xylanases and their industrial applications: a review. Appl Microbiol Biotechnol. 2001 August; 56(3-4):326-38. doi: 10.1007/s002530100704. PMID: 11548999).

DISCLOSURE

Technical Problem

For the convenient use of xylanase employed in various fields, its resistance and activity in harsh conditions (high temperature, basic conditions) are required, but most xylanases have low pH conditions (4.0 to 6.0) and low thermal stability. Therefore, it is difficult to apply xylanase in various fields.

Technical Solution

It is one object of the present disclosure to provide a modified polypeptide having xylanase activity.

It is another object of the present disclosure to provide a composition including the modified polypeptide.

It is still another object of the present disclosure to provide the use of the modified polypeptide or the composition for the reaction with a xylan-containing material.

It is yet another object of the present disclosure to provide a method of degrading xylan-containing materials; and/or a method for producing xylo-oligosaccharides or xylose, including: contacting the modified polypeptide, a host cell expressing the modified polypeptide, and/or a composition including the modified polypeptide with a xylan-containing material.

It is even another object of the present disclosure to provide a polynucleotide encoding the modified polypeptide; a nucleic acid construct including the polynucleotide; a vector containing the polynucleotide or the nucleic acid construct; and/or a host cell containing the polynucleotide, the nucleic acid construct or the vector.

It is further another object of the present disclosure to provide a method for preparing the modified polypeptide.

Advantageous Effects

The modified polypeptide of the present disclosure, which has xylanase activity, can be effectively used in various industrial fields.

BRIEF DESCRIPTION OF THE DRAWINGS

FIGS. 1 to 5 show the results of confirming the thermal stability of the modified polypeptide of the present disclosure.

DETAILED DESCRIPTION OF PREFERRED EMBODIMENTS

One aspect of the present disclosure provides a modified polypeptide having xylanase activity.

In one embodiment, i) the modified polypeptide has a sequence identity of 70% or more and less than 100% with SEQ ID NO: 1; and/or
- ii) the modified polypeptide is a polypeptide encoded by a polynucleotide having a sequence identity of 70% or more and less than 100% with the sequence encoding a mature polypeptide of SEQ ID NO: 1; and/or
- iii) the modified polypeptide is a polypeptide encoded by (a) a mature polypeptide coding sequence of SEQ ID NO: 1, (b) a cDNA thereof, or (c) a polynucleotide that hybridizes to the full-length complement of (a) or (b) under low stringency conditions, medium stringency conditions, medium-high stringency conditions, high stringency conditions, or very high stringency conditions; and/or
- iv) the modified polypeptide is a functional fragment of i), ii) or iii) polypeptide having xylanase activity; and
- the modified polypeptide includes substitution of one or more amino acids at positions 28 and 52 with other amino acids;
- wherein the position number is a position corresponding to the position of the polypeptide of SEQ ID NO: 1.

In one embodiment of any one of the above embodiments, before modification, the amino acid at position 28 may be asparagine (N), and/or the amino acid at position 52 may be asparagine (N).

In one embodiment of any one of the above embodiments, the modified polypeptide may include any one or more modifications below:
- substitution of the amino acid at position 28 with alanine, glycine, or serine; and
- substitution of the amino acid at position 52 with proline, alanine, or glutamate,
- wherein the position number is a position corresponding to the position of the polypeptide of SEQ ID NO: 1.

In one embodiment of any one of the above embodiments, the modified polypeptide may include any one or more substitutions below:
- N28A;
- N28G;
- N28S;
- N52P;
- N52A;
- N52E;
- N28A+N52P;
- N28A+N52A;
- N28A+N52E;
- N28G+N52P;
- N28G+N52A;
- N28G+N52E;
- N28S+N52P;
- N28S+N52A; and
- N28S+N52E.

In one embodiment of any one of the above embodiments, the modified polypeptide may further include substitutions of the amino acids at positions selected from i) to vii) below with cysteine:

i) 3+36;
    ii) 5+34;
    iii) 20+41;
    iv) 3+36+5+34;
    v) 3+36+20+41;
    vi) 5+34+20+41; and
    vii) 3+36+5+34+20+41;
    wherein the position number is a position corresponding
        to the position of the polypeptide of SEQ ID NO: 1.

In one embodiment of any one of the above embodiments, the i) to vii) substitutions may be any one of more modifications selected below:

R3C+T36C;
    S5C+S34C;
    F20C+A41C;
    R3C+T36C+S5C+S34C;
    R3C+T36C+F20C+A41C;
    S5C+S34C+F20C+A41C; and
    R3C+T36C+S5C+S34C+F20C+A41C.

In one embodiment of any one of the above embodiments, the modified polypeptide may include substitutions of two or more amino acids at positions 3, 5, 20, 34, 36, and 41 with cysteine, and form a disulfide bridge between the two substituted amino acids.

In one embodiment of any one of the above embodiments, the modified polypeptide may include substitution of an amino acid pair at positions 3 and 36 with cysteine; substitution of an amino acid pair at positions 5 and 34 with cysteine; and/or substitution of an amino acid pair at positions 20 and 41 with cysteine; and modification of the amino acid pairs to form a disulfide bridge.

In one embodiment of any one of the above embodiments, the modified polypeptide may have increased thermal tolerance and/or thermal stability compared to a polypeptide composed of the amino acid sequence of SEQ ID NO: 1.

Another aspect of the present disclosure provides a composition for the reaction with the modified polypeptide of the present disclosure and/or a xylan-containing material including the modified polypeptide of the present disclosure.

Still another aspect of the present disclosure provides the use of the modified polypeptide and/or a composition including the modified polypeptide for the reaction with a xylan-containing material.

Yet another aspect of the present disclosure provides a method for producing xylo-oligosaccharides or xylose, including: contacting the modified polypeptide, a host cell expressing the modified polypeptide, and/or a composition including the modified polypeptide with a xylan-containing material.

Even another aspect of the present disclosure provides a method of degrading xylan-containing materials, including: treating the modified polypeptide, a host cell expressing the modified polypeptide, and/or a composition including the modified polypeptide to a xylan-containing material.

Further another aspect of the present disclosure provides a polynucleotide encoding the modified polypeptide.

Still further another aspect of the present disclosure provides a nucleic acid construct including the polynucleotide.

Still further another aspect of the present disclosure provides a vector containing the polynucleotide or the nucleic acid construct.

Still further another aspect of the present disclosure provides a host cell including the modified polypeptide, the polynucleotide, the nucleic acid construct, and/or the vector.

Still further another aspect of the present disclosure provides a method for preparing a modified polypeptide, including culturing the host cell.

MODE FOR CARRYING OUT THE INVENTION

Hereinafter, the present disclosure will be described in detail. Meanwhile, each description and embodiment disclosed herein can be applied to other descriptions and embodiments with respect to common features. That is, all combinations of various elements disclosed herein fall within the scope of the present disclosure. Further, the scope of the present disclosure is not limited by the specific description described below.

Additionally, those of ordinary skill in the art may be able to recognize or confirm, using only conventional experimentation, many equivalents to the particular aspects of the invention described herein. Furthermore, it is also intended that these equivalents be included in the present disclosure.

As used in the specification and appended claims, the singular forms ("a", "an", and "the") include plural referents unless the context clearly states otherwise. Unless the context indicates otherwise, singular terms shall include the plural and plural terms shall include the singular. As used in the specification and appended claims, unless stated otherwise, the use of "or" may be used to include "and/or".

As used herein, the term "about" may be presented before a particular numerical value. The term "about" used herein includes not only the exact number recited after the term, but also a range that is near or close to that number. Considering the context in which the number is presented, it can be determined whether any number is close to or near the particular number presented. In one example, the term "about" may refer to a range from −10% to +10% of a numerical value. In another example, the term "about" may refer to a range from −5% to +5% of a given numerical value, but is not limited thereto.

As used herein, the descriptions such as the terms "first, second, third . . . " "i), ii), iii) . . . " or "(a), (b), (c), (d) . . . " are used to distinguish similar constitutions, and these terms do not mean that the constitutions are performed continually or sequentially. For example, when the terms are used in reference to steps of a method, use, or assay, there may be no time interval between these steps, or they may be performed concurrently, or may be performed several seconds, several minutes, several hours, several days, or several months apart.

As used herein, the term "consisting essentially of" may mean that, in the case where the features of the object claimed herein are not substantially affected by the presence of an unspecified component, the unspecified component may be present.

As used herein, the term, "consisting of" means that the total ratio of specific component(s) is 100%. The components or features that are recited after the term "consisting of" may be essential or mandatory. In some embodiments, in addition to the components or features recited after the term "consisting of", any other components or non-essential components may be excluded.

As used herein, the term "comprising/including" means the presence of features, steps or components recited after the term, and does not exclude the presence or addition of one or more features, steps or components. The components or features recited after the term "comprising/including"

herein may be essential or mandatory. However, in some embodiments, the term may further include any other or non-essential components or features.

As used herein, the term "comprising/including" may be modified to refer to "consisting essentially of" or "consisting of" in some embodiments.

With respect to amino acid sequences in the present disclosure, although it is described as a polypeptide "comprising/including" an amino acid sequence described by a specific sequence number, a polypeptide "consisting of" an amino acid sequence described by a specific sequence number, or a protein or polypeptide "having" an amino acid sequence described by a specific sequence number, it is apparent that any protein having an amino acid sequence in which part of the sequence is deleted, modified, substituted, conservative substituted or added can be used in the present disclosure if it has the same or corresponding activity as the polypeptide consisting of the amino acid sequence of the corresponding sequence number. For example, it may be a case where the N-terminus and/or C-terminus of the amino acid sequence is added with a sequence that does not alter the function of the protein, a naturally occurring mutation, a silent mutation thereof, or a conservative substitution, but is not limited thereto.

As used herein, the term "protein" or "polypeptide" refers to a polymer or oligomer of consecutive amino acid residues. In the present disclosure, the "polypeptide", "protein", and "peptide" may be used interchangeably with "amino acid sequence".

In some cases, an amino acid sequence exhibiting activity may be referred to as an "enzyme". In the present disclosure, unless indicated otherwise, amino acid sequences are described in an N-terminal to C-terminal direction.

As used herein, the term "recombinant" with respect to a cell, or nucleic acid, polypeptide, or vector, indicates that the cell, nucleic acid, polypeptide or vector has been modified by the introduction of a heterologous nucleic acid or polypeptide or the alteration of a native nucleic acid or polypeptide, or that the cell is derived from a cell thus modified. Therefore, for example, recombinant cells may express genes that are not found within the native (non-recombinant) form of the cells, or may express native genes that are otherwise abnormally expressed, under expressed or not expressed at all.

As used herein, the term "isolated" refers to a substance which exists in a non-naturally occurring environment or does not exist naturally. It includes substantial isolation of a substance (sequence, enzyme or nucleic acid) from a substance which is naturally associated and found in nature, for example, at least one other component having a sequence, enzyme or nucleic acid.

For example, an isolated sequence, enzyme or nucleic acid provided herein may be provided in a form that is substantially free of one or more contaminants.

Examples of isolated substances include i) any substance that is non-naturally occurring; ii) any substance (e.g., enzyme, variant, nucleic acid, protein, peptide or cofactor) from which one, or more, or all naturally-occurring components associated in nature have been removed; iii) any substance that has been artificially modified from a substance found in nature; or iv) any substance that has been modified to alter the amount of that substance relative to other components associated in nature (e.g., increase in copy number of a gene encoding a specific substance; modification of a promoter naturally linked to a gene encoding a specific substance into a highly active promoter, etc.), but are not limited thereto.

As used herein, the term "wild-type" refers to a naturally-occurring state without artificial modification. When the term "wild-type" is used in reference to a polypeptide, it refers to a naturally occurring polypeptide, which does not have artificial mutations (substitutions, insertions, deletions, etc.) in one or more amino acid positions. Similarly, when the term "wild-type" is used in reference to a polynucleotide, it means not having artificial modifications (substitutions, insertions, deletions) in one or more nucleotides. However, polynucleotides encoding wild-type polypeptides are not limited to wild-type polynucleotides, and include sequences encoding any wild-type polypeptides.

As used herein, the term "parent sequence" or "backbone" refers to a reference sequence in which modification is introduced to create a modified polypeptide. That is, the parent sequence may be served as a starting sequence in which modification such as substitutions, additions, and/or deletions may be introduced. The parent sequence may be naturally-occurring or wild-type, or a variant in which one or more substitutions, insertions or deletions have occurred in the natural or wild type, or may be an artificially synthesized sequence. When the parent sequence is an amino acid sequence exhibiting activity, i.e., an amino acid sequence of an enzyme, it may be referred to as a parent enzyme.

As used herein, the term "reference sequence" means a sequence used to determine the position of amino acids within any amino acid sequence. Any amino acid sequence can be aligned with a reference sequence to determine the position of an amino acid that corresponds to a particular position in the reference sequence within any amino acid sequence.

With respect to amino acid or nucleic acid sequences in the present disclosure, the term "fragment" means a part of a parent sequence. For example, it may be a polypeptide in the form in which one or more amino acids are removed from the C-a or N-terminus of the parent sequence.

As used herein, the term "fragment" of an enzyme may refer to a "functional fragment". The "functional fragment" may also be referred to as an active ingredient, and means a polypeptide that is a part of a parent enzyme and has enzymatic activity of the parent enzyme. For example, the functional fragment of an enzyme may include a catalytic site of the enzyme.

The fragment of the enzyme may include a part of the full length of the parent enzyme. For example, the fragment of the enzyme may include amino acids of at least about 20%, 30%, 40%, 50%, 60%, 70%, 80%, 90%, 95%, 98%, 99% or more, or less than 100% of the full length of the parent enzyme, but is not limited thereto.

As used herein, the term "modifying" means changing or altering. This may be a alternation from a naturally occurring state. In one example, an enzyme can be altered in such a way that the enzyme is altered from a parent or reference sequence.

In the present disclosure, a modified enzyme may be an enzyme that does not exist as it is in nature, i.e., non-naturally occurring.

As used herein, the term "modified" means alternation, e.g., from its naturally occurring form. The modified enzyme of the present disclosure includes non-naturally occurring enzymes or naturally occurring variants. In one example, the modified enzyme of the present disclosure is a modified enzyme that has not been found in nature. In one example, the modified enzyme of the present disclosure may not be one occurring spontaneously, but is not limited thereto.

As used herein, the term "modification", when used with respect to amino acid/nucleic acid sequences, may include substitution of an amino acid/nucleic acid residue of a parent sequence for a different amino acid/nucleic acid residue in one or more positions in an amino acid sequence; deletion of an amino acid/nucleic acid residue (or series of amino acid/nucleic acid residues) of a parent sequence in one or more positions; insertion of an amino acid/nucleic acid residue (or series of amino acid/nucleic acid residues) of a parent sequence in one or more positions; or truncation of the N-terminal and/or C-terminal amino acid sequences, or 5' and/or 3' nucleic acid sequences, and any combination thereof.

As used herein, the term "variant" or "modified polypeptide" of an enzyme refers to a protein having one or more amino acids different from the parent enzyme by conservative substitution and/or modification. The "variant" or "modified polypeptide" may be used interchangeably. The variant or modified polypeptide may be non-naturally occurring, but is not limited thereto. The variant differs from the sequence of the parent enzyme by one or more modifications, e.g., substitutions, deletions and/or insertions of amino acids.

Such variants may generally be identified by modifying one or more amino acids from the parent enzyme and evaluating the properties of the modified protein. That is, the ability of the variants may be enhanced, unchanged or reduced relative to the parent enzyme.

Additionally, some variants may include modified polypeptides in which one or more regions, such as an N-terminal leader sequence or transmembrane domain, have been removed.

Further, other variants may include those in which a region has been removed from the N- and/or C-terminal of a mature protein.

The term "variant" or "modified polypeptide" may be used interchangeably with terms such as modification, modified protein, mutant, mutein, divergent, variant, etc., and is not limited as long as the terms are used to indicate mutation.

The variants may also include deletion or addition of amino acids that have minimal influence on the properties and secondary structure of a polypeptide. For example, the variants may be conjugated with a signal (or leader) sequence at the N-terminal involved in the translocation of proteins co-translationally or post-translationally. Further, the polypeptides may also be conjugated with another sequence or linker to identify, purify, or synthesize the polypeptides.

As used herein, the term "conservative substitution" refers to substitution of an amino acid with another amino acid having similar structural and/or chemical properties. Such amino acid substitution may generally occur based on similarity of polarity, charge, solubility, hydrophobicity, hydrophilicity, and/or amphipathic nature of a residue.

Throughout the entire specification of the present disclosure, the conventional one-letter and three-letter codes for naturally occurring amino acids are used. Additionally, the amino acids mentioned herein are abbreviated according to the nomenclature rules of IUPAC-IUB as follows:

| alanine | Ala, A | arginine | Arg, R |
|---|---|---|---|
| asparagine | Asn, N | aspartic acid | Asp, D |
| cysteine | Cys, C | glutamic acid | Glu, E |
| glutamine | Gln, Q | glycine | Gly, G |
| histidine | His, H | isoleucine | Ile, I |
| leucine | Leu, L | lysine | Lys, K |
| methionine | Met, M | phenylalanine | Phe, F |
| proline | Pro, P | serine | Ser, S |

-continued

| threonine | Thr, T | tryptophan | Trp, W |
|---|---|---|---|
| tyrosine | Tyr, Y | valine | Val, V |

Meanwhile, any amino acid may be described as Xaa or X.

Additionally, three-letter codes generally allowed not only for naturally occurring amino acids, but also for other amino acids, such as 2-Aminoisobutyric acid (Aib), Sar (N-methylglycine), α-methyl-glutamic acid, etc. may be used.

Amino acids may generally be classified based on similarity of polarity, charge, solubility, hydrophobicity, hydrophilicity, and/or amphipathic nature of a residue. Accordingly, amino acid substitution may generally occur based on similarity of polarity, charge, solubility, hydrophobicity, hydrophilicity, and/or amphipathic nature of a residue.

For example, among the amino acids having an electrically charged side chain (electrically charged amino acid), positively charged (basic) amino acids include arginine, lysine, and histidine; negatively charged (acidic) amino acids include glutamic acid and aspartic acid. Further, among the amino acids having an uncharged side chain (uncharged amino acid), nonpolar amino acids include glycine, alanine, valine, leucine, isoleucine, methionine, phenylalanine, tryptophan, and proline; polar or hydrophilic amino acids include serine, threonine, cysteine, tyrosine, asparagine, and glutamine; and among the nonpolar amino acids, aromatic amino acids include phenylalanine, tryptophan and tyrosine.

As used herein, the term "gene" means a polynucleotide that encodes a polypeptide and a polynucleotide including the regions upstream and downstream of the coding region. In some embodiments, a gene may have a sequence (intron) inserted between each coding region (exon).

As used herein, the term "homology" or "identity" refers to a degree of relevance between two given amino acid sequences or nucleotide sequences, and may be expressed as a percentage. The terms homology and identity may often be used interchangeably with each other.

The sequence homology or identity of conserved polynucleotides or polypeptides may be determined by standard alignment algorithms and can be used with a default gap penalty established by the program being used. Substantially, homologous or identical sequences may generally hybridize under moderately or highly stringent conditions to the full-length of the sequence or at least about 50%, 60%, 70%, 80%, or 90% or more of the full-length. It is apparent that hybridization with polynucleotides containing general codon or degenerate codons in hybridizing polynucleotides is also included.

Whether any two polynucleotide or polypeptide sequences have a homology, similarity, or identity may be, for example, determined by a known computer algorithm such as the "FASTA" program (Pearson et al., (1988) [Proc. Natl. Acad. Sci. USA 85]: 2444) using default parameters. Alternatively, it may be determined by the Needleman-Wunsch algorithm (Needleman and Wunsch, 1970, J. Mol. Biol. 48: 443-453), which is performed using the Needleman program of the EMBOSS package (EMBOSS: The European Molecular Biology Open Software Suite, Rice et al., 2000, Trends Genet. 16: 276-277) (version 5.0.0 or versions thereafter) (GCG program package (Devereux, J., et al., Nucleic Acids Research 12: 387 (1984)), BLASTP, BLASTN, FASTA (Atschul, [S.] [F.,] [ET AL.,] J MOLEC BIOL 215]: 403 (1990); Guide to Huge Computers, Martin J. Bishop, [ED.,] Academic Press, San Diego, 1994, and [CARILLO ET al.](1988) SIAM J Applied Math 48: 1073). For example, the homology, similarity, or identity may be determined using BLAST or ClustalW of the National Center for Biotechnology Information (NCBI).

The homology, similarity, or identity of polynucleotides or polypeptides may be, for example, determined by comparing sequence information using, for example, the GAP computer program, such as Needleman et al. (1970), J Mol Biol. 48: 443 as disclosed in Smith and Waterman, Adv. Appl. Math (1981) 2:482. In summary, the GAP program defines the homology, similarity, or identity as the value obtained by dividing the number of similarly aligned symbols (i.e., nucleotides or amino acids) by the total number of the symbols in the shorter of the two sequences. Default parameters for the GAP program may include (1) a unitary comparison matrix (containing a value of 1 for identities and 0 for non-identities) and the weighted comparison matrix of Gribskov et al. (1986), Nucl. Acids Res. 14:6745, as disclosed in Schwartz and Dayhoff, eds., Atlas of Protein Sequence and Structure, National Biomedical Research Foundation, pp. 353-358 (1979) (or EDNAFULL substitution matrix (EMBOSS version of NCBI NUC4.4)); (2) a penalty of 3.0 for each gap and an additional 0.10 penalty for each symbol in each gap (or a gap opening penalty of 10 and a gap extension penalty of 0.5); and (3) no penalty for end gaps.

Further, whether any two polynucleotide or polypeptide sequences have a homology, similarity or identity with each other may be identified by comparing the sequences in a Southern hybridization experiment under stringent conditions as defined, and appropriate hybridization conditions defined are within the skill of the art, and may be determined by a method well known to those skilled in the art (e.g., J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York), but is not limited thereto.

As used herein, the term "mature polypeptide" means a polypeptide in a form without a signal sequence or pro-peptide sequence. A mature protein/polypeptide/peptide may be a functional form of a protein/polypeptide/peptide. The mature polypeptide may be in a final form after translation or post-translational modification. Examples of the post-translational modification include N- or C-terminal modifications, glycosylation, phosphorylation, leader sequence removal etc., but are not limited thereto.

As used herein, the term "nucleic acid construct" refers to a single- or double-stranded nucleic acid molecule, which includes one or more regulatory sequences, and which is artificially synthesized, or engineered to include a specific sequence in a manner that does not exist in nature, or isolated from nature.

As used herein, the term "expression" includes any step involved in the production of a polypeptide, e.g., transcription, post-transcriptional modification, translation, post-translational modification, and secretion, etc. but is not limited thereto.

As used herein, the term "expression vector" refers to a linear or circular nucleic acid molecule including a coding sequence and an operably linked regulatory sequence for expression thereof.

As used herein, the term "operably linked" refers to a constitution of placing a regulatory sequence to an appropriate position to regulate expression of a coding sequence.

Thus, the term "operably linked" includes an attachment or linking between a regulatory region of a functional domain having a known or desired activity such as a promoter, a stop codon, a signal sequence, or an enhancer, and a target (gene or polypeptide) such that the expression, secretion, or function of the target may be regulated in accordance with the known or desired activity.

As used herein, the term "cDNA" refers to a DNA sequence which can be prepared by reverse transcription from a mature, spliced mRNA molecule obtained from a eukaryotic or prokaryotic cell. The cDNA sequence lacks intron sequences that can be present in the corresponding genomic DNA. The initial primary RNA transcript is a precursor to mRNA which is processed through a series of steps including splicing before appearing as mature spliced mRNA.

As used herein, the term "regulatory sequence" refers to a polynucleotide sequence necessary for the expression of a coding sequence. Each regulatory sequence may be native (derived from the same origin) or foreign (derived from different genes) to the coding sequence. Examples of the regulatory sequence may include a leader sequence, a poly-adenylation sequence, a pro-peptide sequence, a promoter, a signal peptide sequence, an operator sequence, a sequence encoding a ribosome-binding domain, and a sequence regulating the termination of transcription and translation. The minimum units of the regulatory sequence may include a promoter, and a sequence for terminating transcription and translation.

In order to describe the variants provided in the present disclosure, the following nomenclature is used.

In the present disclosure, referring to a specific position in an amino acid sequence may include referring to an amino acid present or substituted at that position. Referring to an amino acid at a specific position can be described in various ways. For example, the "position 003" can be described as "position 3", "amino acid 3", "$3^{rd}$ amino acid". Additionally, for example, when the amino acid at position 3 is arginine (R), it may be described as "R3" or "Arg3".

Amino acid substitution can be expressed by describing in the order of the amino acid before substitution, the position, and the amino acid to be substituted. Amino acids can be expressed using the conventional one-letter and three-letter codes. In one example, when serine, an amino acid at position 5 of a specific sequence, is substituted with cysteine, it may be described as "S5C" or "Ser5Cys".

Any amino acid at a specific position may be referred to as "X". For example, X6 refers to any amino acid at position 6. In addition, when the amino acid to be substituted is expressed as X, it means that it is substituted with an amino acid different from the amino acid present before substitution. For example, "V6X" indicates that V at position 6 is substituted with any amino acid other than V.

Different alterations can be expressed by simultaneously describing several types of amino acids using symbols, such as "/" or ",". For example, when the amino acid (F) at position 20 is substituted with S or C, it may be described in combination of F20S/C or F20S,C. As another example, F/S20C means that the amino acid F or S at position 20 before substitution is substituted with C.

Multiple mutations can be described using "+". For example, descriptions such as "R3C+T36C" mean that arginine, an amino acid at position 3, is substituted with cysteine, and threonine, an amino acid at position 8, is substituted with cysteine, respectively.

As used herein, the term "corresponding to" refers to an amino acid residue at the position recited in a protein or peptide, or an amino acid residue which is similar, identical, or homologous to the residue recited in a protein or peptide. Identifying an amino acid at a corresponding position may be determining a particular amino acid in a sequence that refers to a particular sequence. As used herein, the "corresponding region" generally refers to a similar or corresponding position in the related protein or reference protein.

In the present disclosure, the SEQ ID NO: 1 can be used as a reference sequence to determine the position of amino acids in any amino acid sequence.

That is, the SEQ ID NO: 1 disclosed herein can be used to determine the corresponding amino acid residues in any polypeptide having xylanase activity. Unless indicated otherwise in the present disclosure, residues of a particular amino acid sequence are numbered relative to SEQ ID NO: 1.

For example, any amino acid sequence is aligned with SEQ ID NO: 1, and based on the alignment, each amino acid residue of the amino acid sequence can be numbered with reference to the numerical position of the amino acid residue corresponding to the amino acid residue of SEQ ID NO: 1. For example, a sequence alignment algorithm such as that described herein can identify the position of an amino acid or a position where modifications such as substitutions, insertions or deletions occur compared to a query sequence (also referred to as a "reference sequence").

An example of the alignment may be determined by the Needleman-Wunsch algorithm (Needleman and Wunsch, 1970, J. Mol. Biol. 48: 443-453), which is performed using the Needleman program of the EMBOSS package (EM-BOSS: The European Molecular Biology Open Software Suite, Rice et al., 2000, Trends Genet. 16: 276-277), etc., but is not limited thereto.

Additionally, identification of the corresponding amino acid residue in another xylanase can be determined by multiple sequence alignment. Examples of the multiple sequence alignment known in the art include, but are not limited to, programs such as MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, Nucleic Acids Research 30: 3059-3066; Katoh et al., 2005, Nucleic Acids Research 33: 511-518; Katoh and Toh, 2007, Bioinformatics 23: 372-374; Katoh et al., 2009, Methods in Molecular Biology 537: 39-64; Katoh and Toh, 2010, Bioinformatics 26: 1899-1900), and EMBOSS EMMA employing ClustalW (1.83 or later; Thompson et al., 1994, Nucleic Acids Research 22: 4673-4680) using their respective default parameters.

In addition, when enzymes diverged from the mature polypeptide of SEQ ID NO: 1 fail to detect their relationship by traditional sequence-based comparison, other pairwise sequence comparison algorithms can be used (Lindahl and Elofsson, 2000, J. Mol. Biol. 295: 613-615). Greater sensitivity in sequence-based searching can be attained using search programs that utilize probabilistic representations of polypeptide families (profiles) to search databases. For example, the PSI BLAST program generates profiles through an iterative database search process and is capable of detecting remote homologs (Atschul et al., 1997, Nucleic Acids Res. 25: 3389-3402). Even greater sensitivity can be achieved if the family or superfamily for the peptide has one or more representatives in the protein structure databases. Programs such as GenTHREADER (Jones, 1999, J. Mol. Biol. 287: 797-815; McGuffin and Jones, 2003, Bioinformatics 19: 874-881) utilize information from a variety of sources, such as PSI BLAST, secondary structure prediction, structural alignment profiles, and solvation potentials, as input to a neural network that predicts the structural fold for a query sequence. Similarly, the method of Gough et al., 2000, J. Mol. Biol. 313: 903-919 can be used to align a sequence of unknown structure with the superfamily models present in the SCOP database. These alignments can be used in sequence to generate homology models for the peptides, and such models can be assessed for accuracy using a variety of tools developed for that purpose.

For proteins of known structure, several tools and resources are available for retrieving and generating structural alignments. For example, the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, Protein Engineering 11: 739-747), and implementation of these algorithms can additionally be utilized to query structure databases with a structure of interest in order to discover possible structural homologs (Holm and Park, 2000, Bioinformatics 16: 566-567).

The above methods are one exemplary, and are not limited thereto.

Hereinafter, the specific embodiments of the present disclosure will be described in more detail.

As used herein, xylanase refers to an enzyme that catalyzes endohydrolysis of 1,4-beta-D-xylosidic bonds in xylan. For example, it may be an enzyme having an EC number of 3.2.1.8, but is not limited thereto.

In the present disclosure, xylanase activity can be measured and evaluated using methods known in the art, including the embodiments described herein.

As used herein, the term "parent xylanase" refers to xylanase to which modification is applied to produce the variant or the modified polypeptide of the present disclosure. Specifically, the parent xylanase, parent enzyme, or parent sequence may be a naturally occurring polypeptide or a wild-type polypeptide, may be a mature polypeptide thereof, and may include a variant or functional fragment thereof, but is not limited thereto, as long as the polypeptide has xylanase activity and can be a parent of the variant.

The parent xylanase provided in the present disclosure may be a polypeptide of SEQ ID NO: 1, but is not limited thereto. Additionally, it may be a polypeptide having a sequence identity of about 60%, 70%, 75%. 80%. 85%, 90%, 95%, 96%, 97%, 98% or 99% or more with the polypeptide of SEQ ID NO: 1 as long as it has xylanase activity, and any polypeptide may be included within the scope of the parent xylanase as long as it has the same or corresponding activity to the polypeptide consisting of the amino acid sequence of SEQ ID NO: 1.

The parent xylanase of the variant provided herein may be derived from *Orpinomyces* sp., *Neocallimastix* sp., *Piromyces* sp., or Ruminococcus sp. Specifically, it may be derived from *Orpinomyces* sp.

Meanwhile, the above-described microorganism is an exemplary of microorganisms from which the xylanase provided herein can be derived, and includes those derived from microorganisms taxonomically homologous to the microorganism regardless of the name of the microorganisms.

The above-described microorganism may be obtained from known microorganism depositary authorities such as ATCC, DSMZ, CBS, NRRL, KCTC, and KCCM.

As used herein, a sequence "derived from" a specific microorganism is not limited to those naturally produced or producible in that microorganism, but also includes sequences encoded by genes produced and isolated from the microorganism containing the genes.

For example, xylanase derived from *Orpinomyces* sp. may include not only enzymes having xylanase activity naturally produced by the microorganisms of *Orpinomyces* sp., but also those produced in other host cells through genetic modifications known in the art (e.g., transformation into a sequence encoding the enzyme).

As used herein, the "modified polypeptide having xylanase activity" may be a variant of a parent xylanase.

As used herein, the term "variant of a parent xylanase" or "xylanase variant" refers to a protein having xylanase activity with at least one amino acid different from the amino acid sequence of the parent xylanase.

The "modified polypeptide having xylanase activity", "variant of a parent xylanase" and "xylanase variant" can be used interchangeably.

The variant provided in the present disclosure may include one or more amino acid modifications in the sequences of the parent xylanase, while having xylanase activity. The modification may be an amino acid substitution and/or disulfide bond formation.

Additionally, i) the modified polypeptide may be a polypeptide having a sequence identity of 70% or more and less than 100% with SEQ ID NO: 1; and/or ii) the variant may be a polypeptide encoded by a polynucleotide having a sequence identity of 70% or more and less than 100% with the sequence encoding a mature polypeptide of SEQ ID NO: 1; and/or iii) the variant may be a polypeptide encoded by (a) a mature polypeptide coding sequence of SEQ ID NO: 1, (b) a cDNA thereof, or (c) a polynucleotide that hybridizes to the full-length complement of (a) or (b) under low stringency conditions, medium stringency conditions, medium-high stringency conditions, high stringency conditions, or very high stringency conditions; and/or iv) the variant may be a functional fragment of i), ii) or iii) polypeptide having xylanase activity.

Specifically, the variant provided in the present disclosure includes modification of one or more amino acids in the parent xylanase sequence while having xylanase activity, and thus may have one or more modified functions or properties compared to the parent xylanase.

In one embodiment, the variant provided in the present disclosure includes modification of one or more amino acids in the parent xylanase sequence while having xylanase activity, and thus may have one or more modified functions or properties compared to the parent xylanase and one or more conservative substitutions.

The variant provided in the present disclosure, being a variant of the parent xylanase, may be a polypeptide having xylanase activity.

In one embodiment, the variant provided in the present disclosure may include modifications at one or more positions corresponding to positions 28 and 52 of SEQ ID NO: 1.

In the present disclosure, the position number is a position corresponding to the position of the polypeptide of SEQ ID NO: 1, and the term "corresponding" is as described above.

In one embodiment, the variant provided in the present disclosure may include modifications of amino acids corresponding to one or more of N28 and N52 of SEQ ID NO: 1.

In one embodiment, before the modification of the variant provided in the present disclosure, the amino acid at position 28 may be asparagine (N); and/or the amino acid at position 52 may be asparagine (N).

In one embodiment, the variant provided in the present disclosure may include substitution of the amino acid corresponding to position 28 of SEQ ID NO: 1 with G, A, V, L, I, M, F, W, P, S, T, C, Y, Q, D, E, K, R or H. Specifically, it may include substitution with G, A, V, L, I, M, F, W, P, S, T, C, Y or Q, and more specifically, substitution with A, G, or S.

In one embodiment, the variant provided in the present disclosure may include substitution of the amino acid corresponding to position 52 of SEQ ID NO: 1 with G, A, V, L, I, M, F, W, P, S, T, C, Y, Q, D, E, K, R or H. Specifically, it may include substitution with G, A, V, L, I, M, F, W, P, D, E, K, R or H, and more specifically, substitution with P, A, or E.

In one embodiment, the variant provided in the present disclosure may include substitution of the amino acid corresponding to position 28 of SEQ ID NO: 1 with a hydrophobic or polar amino acid.

In one embodiment, the variant provided in the present disclosure may include substitution of the amino acid corresponding to position 52 of SEQ ID NO: 1 with a hydrophobic or acidic amino acid.

In one embodiment, the variant provided in the present disclosure may include one or more substitutions among N28A/G/S and N52P/A/E of SEQ ID NO: 1.

In one embodiment, the variant provided in the present disclosure includes all possible combinations of the modifications described above.

For example, the variant may include modifications of the amino acids at positions selected below, by combinations of the modifications described above:

N52P;
N52A;
N52E;
N28A;
N28G;
N28S;
N28A+N52P;
N28A+N52A;
N28A+N52E;
N28G+N52P;
N28G+N52A;
N28G+N52E;
N28S+N52P;
N28S+N52A; and
N28S+N52E.

In one embodiment, the variant provided in the present disclosure may further include modifications at one or more positions corresponding to the positions 3, 5, 20, 34, 36, and 41 of SEQ ID NO: 1.

In one embodiment, the variant provided in the present disclosure may include modifications of amino acids at positions selected from i) to vii) below:

i) 3+36;
ii) 5+34;
iii) 20+41;
iv) 3+36+5+34;
v) 3+36+20+41;
vi) 5+34+20+41; and
vii) 3+36+5+34+20+41.

In present disclosure, the position number is a position corresponding to the position of the polypeptide of SEQ ID NO: 1, and the "corresponding" is as described above.

In one embodiment, the variant provided in the present disclosure may include modifications of amino acids corresponding to one or more among R3, S5, F20, S34, T36, and A41 of SEQ ID NO: 1.

In one embodiment, before the modification provided in the present disclosure, the amino acid corresponding to position 3 of SEQ ID NO: 1 may be arginine (R); the amino acid corresponding to position 5 may be serine (S); the amino acid corresponding to position 20 may be phenylalanine (F); the amino acid corresponding to position 34 may be serine (S); the amino acid corresponding to position 36 may be threonine (T); and/or the amino acid corresponding to position 41 may be alanine (A).

In one embodiment, the variant provided in the present disclosure may include substitution of the amino acid corresponding to position 3 of SEQ ID NO: 1 with G, A, V, L, I, M, F, W, P, S, T, C, Y, N, Q, D, E, K, or H. Specifically, it may include substitution with S, T, C, Y, N, or Q, and more specifically, substitution with C.

In one embodiment, the variant provided in the present disclosure may include substitution of the amino acid corresponding to position 5 of SEQ ID NO: 1 with G, A, V, L, I, M, F, W, P, T, C, Y, N, Q, D, E, K, R, or H. Specifically, it may include substitution with T, C, Y, N, or Q, and more specifically, substitution with C.

In one embodiment, the variant provided in the present disclosure may include substitution of the amino acid corresponding to position 20 of SEQ ID NO: 1 with G, A, V, L, I, M, W, P, S, T, C, Y, N, Q, D, E, K, R, or H. Specifically, it may include substitution with S, T, C, Y, N, or Q, and more specifically, substitution with C.

In one embodiment, the variant provided in the present disclosure may include substitution of the amino acid corresponding to position 34 of SEQ ID NO: 1 with G, A, V, L, I, M, F, W, P, T, C, Y, N, Q, D, E, K, R, or H. Specifically, it may include substitution with T, C, Y, N, or Q, and more specifically, substitution with C.

In one embodiment, the variant provided in the present disclosure may include substitution of the amino acid corresponding to position 36 of SEQ ID NO: 1 with G, A, V, L, I, M, F, W, P, S, C, Y, N, Q, D, E, K, R, or H. Specifically, it may include substitution with S, C, Y, N, or Q, and more specifically, substitution with C.

In one embodiment, the variant provided in the present disclosure may include substitution of the amino acid corresponding to position 41 of SEQ ID NO: 1 with G, V, L, I, M, F, W, P, S, T, C, Y, N, Q, D, E, K, R, or H. Specifically, it may include substitution with S, T, C, Y, N, or Q, and more specifically, substitution with C.

In one embodiment, the variant provided in the present disclosure may include substitution of the amino acid corresponding to position 3 of SEQ ID NO: 1 with a polar amino acid.

In one embodiment, the variant provided in the present disclosure may include substitution of the amino acid corresponding to position 5 of SEQ ID NO: 1 with a polar amino acid.

In one embodiment, the variant provided in the present disclosure may include substitution of the amino acid corresponding to position 20 of SEQ ID NO: 1 with a polar amino acid.

In one embodiment, the variant provided in the present disclosure may include substitution of the amino acid corresponding to position 34 of SEQ ID NO: 1 with a polar amino acid.

In one embodiment, the variant provided in the present disclosure may include substitution of the amino acid corresponding to position 36 of SEQ ID NO: 1 with a polar amino acid.

In one embodiment, the variant provided in the present disclosure may include substitution of the amino acid corresponding to position 41 of SEQ ID NO: 1 with a polar amino acid.

In one embodiment, the variant provided in the present disclosure may include one or more substitutions among R3C, S5C, F20C, S34C, T36C, and A41C of SEQ ID NO: 1.

In one embodiment, the variant provided in the present disclosure may include two or more substitutions among R3C, S5C, F20C, S34C, T36C, and A41C of SEQ ID NO: 1.

In one embodiment, the variant provided in the present disclosure may include any one or more substitutions selected from the following:

R3C+T36C;
S5C+S34C;
F20C+A41C;
R3C+T36C+S5C+S34C;
R3C+T36C+F20C+A41C;
S5C+S34C+F20C+A41C; and
R3C+T36C+S5C+S34C+F20C+A41C.

In one embodiment, the variant may include any one or more substitutions of the following i) to vi): i) substitution of the amino acid at position 3 with cysteine; ii) substitution of the amino acid at position 5 with cysteine; iii) substitution of the amino acid at position 20 with cysteine; iv) substitution of the amino acid at position 34 with cysteine; v) substitution of the amino acid at position 36 with cysteine; and vi) substitution of the amino acid at position 41 with cysteine, but is not limited thereto.

In one embodiment, the variant provided in the present disclosure may include substitutions of amino acids corresponding to two or more of positions 3, 5, 20, 34, 36, and 41 of SEQ ID NO: 1 with cysteine and form a disulfide bridge between the two substituted amino acids.

In one embodiment, the variant provided in the present disclosure may include substitutions of an amino acid pair at positions 3 and 36; an amino acid pair at positions 5 and 34; and/or an amino acid pair at positions 20 and 41 with cysteine; and the amino acid pairs may form a disulfide bridge.

In one embodiment, the variant provided in the present disclosure includes all possible combinations of the modifications described above.

For example, the variant may include modifications of amino acids at positions selected below, by combinations of the modifications described above:

28
52
3
5
20
34
36
41
28+52
28+3
28+5
28+20
28+34
28+36
28+41

52+3
52+5
52+20
52+34
52+36
52+41
3+5
3+20
3+34
3+36
3+41
5+20
5+34
5+36
5+41
20+34
20+36
20+41
34+36
34+41
36+41
28+52+3
28+52+5
28+52+20
28+52+34
28+52+36
28+52+41
28+3+5
28+3+20
28+3+34
28+3+36
28+3+41
28+5+20
28+5+34
28+5+36
28+5+41
28+20+34
28+20+36
28+20+41
28+34+36
28+34+41
28+36+41
52+3+5
52+3+20
52+3+34
52+3+36
52+3+41
52+5+20
52+5+34
52+5+36
52+5+41
52+20+34
52+20+36
52+20+41
52+34+36
52+34+41
52+36+41
3+5+20
3+5+34
3+5+36
3+5+41
3+20+34
3+20+36
3+20+41
3+34+36
3+34+41
3+36+41

5+20+34
5+20+36
5+20+41
5+34+36
5+34+41
5+36+41
20+34+36
20+34+41
20+36+41
34+36+41
28+52+3+5
28+52+3+20
28+52+3+34
28+52+3+36
28+52+3+41
28+52+5+20
28+52+5+34
28+52+5+36
28+52+5+41
28+52+20+34
28+52+20+36
28+52+20+41
28+52+34+36
28+52+34+41
28+52+36+41
28+3+5+20
28+3+5+34
28+3+5+36
28+3+5+41
28+3+20+34
28+3+20+36
28+3+20+41
28+3+34+36
28+3+34+41
28+3+36+41
28+5+20+34
28+5+20+36
28+5+20+41
28+5+34+36
28+5+34+41
28+5+36+41
28+20+34+36
28+20+34+41
28+20+36+41
28+34+36+41
52+3+5+20
52+3+5+34
52+3+5+36
52+3+5+41
52+3+20+34
52+3+20+36
52+3+20+41
52+3+34+36
52+3+34+41
52+3+36+41
52+5+20+34
52+5+20+36
52+5+20+41
52+5+34+36
52+5+34+41
52+5+36+41
52+20+34+36
52+20+34+41
52+20+36+41
52+34+36+41
3+5+20+34
3+5+20+36

3+5+20+41
3+5+34+36
3+5+34+34
3+5+36+41
3+20+34+36
3+20+34+41
3+20+36+41
3+34+36+41
5+20+34+36
5+20+34+41
5+20+36+41
5+34+36+41
20+34+36+41
28+52+3+5+20
28+52+3+5+34
28+52+3+5+36
28+52+3+5+41
28+52+3+20+34
28+52+3+20+36
28+52+3+20+41
28+52+3+34+36
28+52+3+34+41
28+52+3+36+41
28+52+5+20+34
28+52+5+20+36
28+52+5+20+41
28+52+5+34+36
28+52+5+34+41
28+52+5+36+41
28+52+20+34+36
28+52+20+34+41
28+52+20+36+41
28+52+34+36+41
28+3+5+20+34
28+3+5+20+36
28+3+5+20+41
28+3+5+34+36
28+3+5+34+41
28+3+5+36+41
28+3+20+34+36
28+3+20+34+41
28+3+20+36+41
28+3+34+36+41
28+5+20+34+36
28+5+20+34+41
28+5+20+36+41
28+5+34+36+41
28+20+34+36+41
52+3+5+20+34
52+3+5+20+36
52+3+5+20+41
52+3+5+34+36
52+3+5+34+41
52+3+5+36+41
52+3+20+34+36
52+3+20+34+41
52+3+20+36+41
52+3+34+36+41
52+5+20+34+36
52+5+20+34+41
52+5+20+36+41
52+5+34+36+41
52+20+34+36+41
3+5+20+34+36
3+5+20+34+41
3+5+20+36+41
3+5+34+36+41

3+20+34+36+41
5+20+34+36+41
28+52+3+5+20+34
28+52+3+5+20+36
28+52+3+5+20+41
28+52+3+5+34+36
28+52+3+5+34+41
28+52+3+5+36+41
28+52+3+20+34+36
28+52+3+20+34+41
28+52+3+20+36+41
28+52+3+34+36+41
28+52+5+20+34+36
28+52+5+20+34+41
28+52+5+20+36+41
28+52+5+34+36+41
28+52+20+34+36+41
28+3+5+20+34+36
28+3+5+20+34+41
28+3+5+20+36+41
28+3+5+34+36+41
28+3+20+34+36+41
28+5+20+34+36+41
52+3+5+20+34+36
52+3+5+20+34+41
52+3+5+20+36+41
52+3+5+34+36+41
52+3+20+34+36+41
52+5+20+34+36+41
3+5+20+34+36+41
28+52+3+5+20+34+36
28+52+3+5+20+34+41
28+52+3+5+20+36+41
28+52+3+5+34+36+41
28+52+3+20+34+36+41
28+52+5+20+34+36+41
28+3+5+20+34+36+41
52+3+5+20+34+36+41, and
28+52+3+5+20+34+36+41.

In another example, the variant may include one or more modifications selected from the following, but is not limited thereto:

N28A/G/S
N52P/A/E
R3C
S5C
F20C
S34C
T36C
A41C
N28A/G/S+N52P/A/E
N28A/G/S+R3C
N28A/G/S+S5C
N28A/G/S+F20C
N28A/G/S+S34C
N28A/G/S+T36C
N28A/G/S+A41C
N52P/A/E+R3C
N52P/A/E+S5C
N52P/A/E+F20C
N52P/A/E+S34C
N52P/A/E+T36C
N52P/A/E+A41C
R3C+S5C
R3C+F20C
R3C+S34C
R3C+T36C

R3C+A41C
S5C+F20C
S5C+S34C
S5C+T36C
S5C+A41C
F20C+S34C
F20C+T36C
F20C+A41C
S34C+T36C
S34C+A41C
T36C+A41C
N28A/G/S+N52P/A/E+R3C
N28A/G/S+N52P/A/E+S5C
N28A/G/S+N52P/A/E+F20C
N28A/G/S+N52P/A/E+S34C
N28A/G/S+N52P/A/E+T36C
N28A/G/S+N52P/A/E+A41C
N28A/G/S+R3C+S5C
N28A/G/S+R3C+F20C
N28A/G/S+R3C+S34C
N28A/G/S+R3C+T36C
N28A/G/S+R3C+A41C
N28A/G/S+S5C+F20C
N28A/G/S+S5C+S34C
N28A/G/S+S5C+T36C
N28A/G/S+S5C+A41C
N28A/G/S+F20C+S34C
N28A/G/S+F20C+T36C
N28A/G/S+F20C+A41C
N28A/G/S+S34C+T36C
N28A/G/S+S34C+A41C
N28A/G/S+T36C+A41C
N52P/A/E+R3C+S5C
N52P/A/E+R3C+F20C
N52P/A/E+R3C+S34C
N52P/A/E+R3C+T36C
N52P/A/E+R3C+A41C
N52P/A/E+S5C+F20C
N52P/A/E+S5C+S34C
N52P/A/E+S5C+T36C
N52P/A/E+S5C+A41C
N52P/A/E+F20C+S34C
N52P/A/E+F20C+T36C
N52P/A/E+F20C+A41C
N52P/A/E+S34C+T36C
N52P/A/E+S34C+A41C
N52P/A/E+T36C+A41C
R3C+S5C+F20C
R3C+S5C+S34C
R3C+S5C+T36C
R3C+S5C+A41C
R3C+F20C+S34C
R3C+F20C+T36C
R3C+F20C+A41C
R3C+S34C+T36C
R3C+S34C+A41C
R3C+T36C+A41C
S5C+F20C+S34C
S5C+F20C+T36C
S5C+F20C+A41C
S5C+S34C+T36C
S5C+S34C+A41C
S5C+T36C+A41C
F20C+S34C+T36C
F20C+S34C+A41C
F20C+T36C+A41C
S34C+T36C+A41C

N28A/G/S+N52P/A/E+R3C+S5C
N28A/G/S+N52P/A/E+R3C+F20C
N28A/G/S+N52P/A/E+R3C+S34C
N28A/G/S+N52P/A/E+R3C+T36C
N28A/G/S+N52P/A/E+R3C+A41C
N28A/G/S+N52P/A/E+S5C+F20C
N28A/G/S+N52P/A/E+S5C+S34C
N28A/G/S+N52P/A/E+S5C+T36C
N28A/G/S+N52P/A/E+S5C+A41C
N28A/G/S+N52P/A/E+F20C+S34C
N28A/G/S+N52P/A/E+F20C+T36C
N28A/G/S+N52P/A/E+F20C+A41C
N28A/G/S+N52P/A/E+S34C+T36C
N28A/G/S+N52P/A/E+S34C+A41C
N28A/G/S+N52P/A/E+T36C+A41C
N28A/G/S+R3C+S5C+F20C
N28A/G/S+R3C+S5C+S34C
N28A/G/S+R3C+S5C+T36C
N28A/G/S+R3C+S5C+A41C
N28A/G/S+R3C+F20C+S34C
N28A/G/S+R3C+F20C+T36C
N28A/G/S+R3C+F20C+A41C
N28A/G/S+R3C+S34C+T36C
N28A/G/S+R3C+S34C+A41C
N28A/G/S+R3C+T36C+A41C
N28A/G/S+S5C+F20C+S34C
N28A/G/S+S5C+F20C+T36C
N28A/G/S+S5C+F20C+A41C
N28A/G/S+S5C+S34C+T36C
N28A/G/S+S5C+S34C+A41C
N28A/G/S+S5C+T36C+A41C
N28A/G/S+F20C+S34C+T36C
N28A/G/S+F20C+S34C+A41C
N28A/G/S+F20C+T36C+A41C
N28A/G/S+S34C+T36C+A41C
N52P/A/E+R3C+S5C+F20C
N52P/A/E+R3C+S5C+S34C
N52P/A/E+R3C+S5C+T36C
N52P/A/E+R3C+S5C+A41C
N52P/A/E+R3C+F20C+S34C
N52P/A/E+R3C+F20C+T36C
N52P/A/E+R3C+F20C+A41C
N52P/A/E+R3C+S34C+T36C
N52P/A/E+R3C+S34C+A41C
N52P/A/E+R3C+T36C+A41C
N52P/A/E+S5C+F20C+S34C
N52P/A/E+S5C+F20C+T36C
N52P/A/E+S5C+F20C+A41C
N52P/A/E+S5C+S34C+T36C
N52P/A/E+S5C+S34C+A41C
N52P/A/E+S5C+T36C+A41C
N52P/A/E+F20C+S34C+T36C
N52P/A/E+F20C+S34C+A41C
N52P/A/E+F20C+T36C+A41C
N52P/A/E+S34C+T36C+A41C
R3C+S5C+F20C+S34C
R3C+S5C+F20C+T36C
R3C+S5C+F20C+A41C
R3C+S5C+S34C+T36C
R3C+S5C+S34C+A41C
R3C+S5C+T36C+A41C
R3C+F20C+S34C+T36C
R3C+F20C+S34C+A41C
R3C+F20C+T36C+A41C
R3C+S34C+T36C+A41C
S5C+F20C+S34C+T36C
S5C+F20C+S34C+A41C

S5C+F20C+T36C+A41C
S5C+S34C+T36C+A41C
F20C+S34C+T36C+A41C
N28A/G/S+N52P/A/E+R3C+S5C+F20C
N28A/G/S+N52P/A/E+R3C+S5C+S34C
N28A/G/S+N52P/A/E+R3C+S5C+T36C
N28A/G/S+N52P/A/E+R3C+S5C+A41C
N28A/G/S+N52P/A/E+R3C+F20C+S34C
N28A/G/S+N52P/A/E+R3C+F20C+T36C
N28A/G/S+N52P/A/E+R3C+F20C+A41C
N28A/G/S+N52P/A/E+R3C+S34C+T36C
N28A/G/S+N52P/A/E+R3C+S34C+A41C
N28A/G/S+N52P/A/E+R3C+T36C+A41C
N28A/G/S+N52P/A/E+S5C+F20C+S34C
N28A/G/S+N52P/A/E+S5C+F20C+T36C
N28A/G/S+N52P/A/E+S5C+F20C+A41C
N28A/G/S+N52P/A/E+S5C+S34C+T36C
N28A/G/S+N52P/A/E+S5C+S34C+A41C
N28A/G/S+N52P/A/E+S5C+T36C+A41C
N28A/G/S+N52P/A/E+F20C+S34C+T36C
N28A/G/S+N52P/A/E+F20C+S34C+A41C
N28A/G/S+N52P/A/E+F20C+T36C+A41C
N28A/G/S+N52P/A/E+S34C+T36C+A41C
N28A/G/S+R3C+S5C+F20C+S34C
N28A/G/S+R3C+S5C+F20C+T36C
N28A/G/S+R3C+S5C+F20C+A41C
N28A/G/S+R3C+S5C+S34C+T36C
N28A/G/S+R3C+S5C+S34C+A41C
N28A/G/S+R3C+S5C+T36C+A41C
N28A/G/S+R3C+F20C+S34C+T36C
N28A/G/S+R3C+F20C+S34C+A41C
N28A/G/S+R3C+F20C+T36C+A41C
N28A/G/S+R3C+S34C+T36C+A41C
N28A/G/S+S5C+F20C+S34C+T36C
N28A/G/S+S5C+F20C+S34C+A41C
N28A/G/S+S5C+F20C+T36C+A41C
N28A/G/S+S5C+S34C+T36C+A41C
N28A/G/S+F20C+S34C+T36C+A41C
N52P/A/E+R3C+S5C+F20C+S34C
N52P/A/E+R3C+S5C+F20C+T36C
N52P/A/E+R3C+S5C+F20C+A41C
N52P/A/E+R3C+S5C+S34C+T36C
N52P/A/E+R3C+S5C+S34C+A41C
N52P/A/E+R3C+S5C+T36C+A41C
N52P/A/E+R3C+F20C+S34C+T36C
N52P/A/E+R3C+F20C+S34C+A41C
N52P/A/E+R3C+F20C+T36C+A41C
N52P/A/E+R3C+S34C+T36C+A41C
N52P/A/E+S5C+F20C+S34C+T36C
N52P/A/E+S5C+F20C+S34C+A41C
N52P/A/E+S5C+F20C+T36C+A41C
N52P/A/E+S5C+S34C+T36C+A41C
N52P/A/E+F20C+S34C+T36C+A41C
R3C+S5C+F20C+S34C+T36C
R3C+S5C+F20C+S34C+A41C
R3C+S5C+F20C+T36C+A41C
R3C+S5C+S34C+T36C+A41C
R3C+F20C+S34C+T36C+A41C
S5C+F20C+S34C+T36C+A41C
N28A/G/S+N52P/A/E+R3C+S5C+F20C+S34C
N28A/G/S+N52P/A/E+R3C+S5C+F20C+T36C
N28A/G/S+N52P/A/E+R3C+S5C+F20C+A41C
N28A/G/S+N52P/A/E+R3C+S5C+S34C+T36C
N28A/G/S+N52P/A/E+R3C+S5C+S34C+A41C
N28A/G/S+N52P/A/E+R3C+S5C+T36C+A41C
N28A/G/S+N52P/A/E+R3C+F20C+S34C+T36C
N28A/G/S+N52P/A/E+R3C+F20C+S34C+A41C

N28A/G/S+N52P/A/E+R3C+F20C+T36C+A41C
N28A/G/S+N52P/A/E+R3C+S34C+T36C+A41C
N28A/G/S+N52P/A/E+S5C+F20C+S34C+T36C
N28A/G/S+N52P/A/E+S5C+F20C+S34C+A41C
N28A/G/S+N52P/A/E+S5C+F20C+T36C+A41C
N28A/G/S+N52P/A/E+S5C+S34C+T36C+A41C
N28A/G/S+N52P/A/E+F20C+S34C+T36C+A41C
N28A/G/S+R3C+S5C+F20C+S34C+T36C
N28A/G/S+R3C+S5C+F20C+S34C+A41C
N28A/G/S+R3C+S5C+F20C+T36C+A41C
N28A/G/S+R3C+S5C+S34C+T36C+A41C
N28A/G/S+R3C+F20C+S34C+T36C+A41C
N28A/G/S+S5C+F20C+S34C+T36C+A41C
N52P/A/E+R3C+S5C+F20C+S34C+T36C
N52P/A/E+R3C+S5C+F20C+S34C+A41C
N52P/A/E+R3C+S5C+F20C+T36C+A41C
N52P/A/E+R3C+S5C+S34C+T36C+A41C
N52P/A/E+R3C+F20C+S34C+T36C+A41C
N52P/A/E+S5C+F20C+S34C+T36C+A41C
R3C+S5C+F20C+S34C+T36C+A41C
N28A/G/S+N52P/A/E+R3C+S5C+F20C+S34C+T36C
N28A/G/S+N52P/A/E+R3C+S5C+F20C+S34C+A41C
N28A/G/S+N52P/A/E+R3C+S5C+F20C+T36C+A41C
N28A/G/S+N52P/A/E+R3C+S5C+S34C+T36C+A41C
N28A/G/S+N52P/A/E+R3C+F20C+S34C+T36C+A41C
N28A/G/S+N52P/A/E+S5C+F20C+S34C+T36C+A41C
N28A/G/S+R3C+S5C+F20C+S34C+T36C+A41C
N52P/A/E+R3C+S5C+F20C+S34C+T36C+A41C, and
N28A/G/S+N52P/A/E+R3C+S5C+F20C+S34C+T36C+
    A41C.

Specifically, the variant including the R3C+T36C substitution of SEQ ID NO: 1 may be represented by SEQ ID NO: 3; the variant including the S5C+S34C substitution of SEQ ID NO: 1 may be represented by SEQ ID NO: 5; the variant including the F20C+A41C substitution of SEQ ID NO: 1 may be represented by SEQ ID NO: 7; the variant including the R3C+T36C+N52P substitution of SEQ ID NO: 1 may be represented by SEQ ID NO: 9; the variant including the R3C+T36C+N28G substitution of SEQ ID NO: 1 may be represented by SEQ ID NO: 11; the variant including the R3C+T36C+N52P+N28G substitution of SEQ ID NO: 1 may be represented by SEQ ID NO: 13; the variant including the S5C+S34C+N52P substitution of SEQ ID NO: 1 may be represented by SEQ ID NO: 15; the variant including the S5C+S34C+N28G substitution of SEQ ID NO: 1 may be represented by SEQ ID NO: 17; the variant including the S5C+S34C+N52P+N28G substitution of SEQ ID NO: 1 may be represented by SEQ ID NO: 19; the variant including the F20C+A41+N52P substitution of SEQ ID NO: 1 may be represented by SEQ ID NO: 21; the variant including the F20C+A41C+N28G substitution of SEQ ID NO: 1 may be represented by SEQ ID NO: 23; and the variant including the F20C+A41C+N52P+N28G substitution of SEQ ID NO: 1 may be represented by SEQ ID NO: 25.

In one embodiment, the variant provided in the present disclosure may have a sequence identity of about 60% or more, for example, 65% or more, 70% or more, 75% or more, 80% or more, 85% or more, 90% or more, 91% or more, 92% or more, 93% or more, 94% or more, 95% or more, 96% or more, 97% or more, 98% or more, or 99% or more, but less than 100% with the parent xylanase; a mature polypeptide thereof, or a functional fragment thereof.

In one embodiment, the variant provided in the present disclosure may have a sequence identity of about 60% or more, for example, 65% or more, 70% or more, 75% or more, 80% or more, 85% or more, 90% or more, 91% or more, 92% or more, 93% or more, 94% or more, 95% or more, 96% or more, 97% or more, 98% or more, or 99% or more, but less than 100% with SEQ ID NO: 1.

In one embodiment, the variant provided in the present disclosure may be a polypeptide encoded by a polynucleotide having a sequence identity of about 60% or more, for example, 65% or more, 70% or more, 75% or more, 80% or more, 85% or more, 90% or more, 91% or more, 92% or more, 93% or more, 94% or more, 95% or more, 96% or more, 97% or more, 98% or more, or 99% or more, but less than 100% with a sequence encoding a mature polypeptide of SEQ ID NO: 1.

In one embodiment, the variant provided in the present disclosure may be a polypeptide encoded by (a) a mature polypeptide coding sequence of SEQ ID NO: 1, (b) a cDNA thereof, or (c) a polynucleotide that hybridizes to the full-length complement of (a) or (b) under low stringency conditions, medium stringency conditions, medium-high stringency conditions, high stringency conditions, or very high stringency conditions.

In one embodiment, the variant provided in the present disclosure may have a sequence identity of about 60% or more, for example, 65% or more, 70% or more, 75% or more, 80% or more, 85% or more, 90% or more, 91% or more, 92% or more, 93% or more, 94% or more, 95% or more, 96% or more, 97% or more, 98% or more, or 99% or more, but less than 100% with a functional fragment of SEQ ID NO: 1.

In one embodiment, the variant provided in the present disclosure may be a polypeptide encoded by a polynucleotide having a nucleotide sequence identity of about 60% or more, for example, 65% or more, 70% or more, 75% or more, 80% or more, 85% or more, 90% or more, 91% or more, 92% or more, 93% or more, 94% or more, 95% or more, 96% or more, 97% or more, 98% or more, or 99% or more, but less than 100% with a nucleotide sequence represented by SEQ ID NO: 2.

In one embodiment, the variant provided in the present disclosure may be a polypeptide represented by SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, or SEQ ID NO: 25.

In one embodiment, the variant provided in the present disclosure may be a polypeptide in which the amino acids at one or more positions 28, 52, 3, 5, 20, 34, 36, and 41 in the amino acid sequences of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, or SEQ ID NO: 25 are fixed, and which has a sequence identity of about 60% or more, for example, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more, or 100% with the amino acid sequences of SEQ ID NOS above, a mature polypeptide thereof, or a functional fragment thereof.

In one embodiment, the variant provided in the present disclosure may be encoded by a polynucleotide represented by SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, or SEQ ID NO: 26.

In one embodiment, the variant including the R3C+T36C substitution of SEQ ID NO: 1 may be encoded by a polynucleotide represented by SEQ ID NO: 4; the variant including the S5C+S34C substitution of SEQ ID NO: 1 may be encoded by a polynucleotide represented by SEQ ID NO: 6; the variant including the F20C+A41C substitution of SEQ ID NO: 1 may be encoded by a polynucleotide represented by SEQ ID NO: 8; the variant including the R3C+T36C+N52P substitution of SEQ ID NO: 1 may be encoded by a polynucleotide represented by SEQ ID NO: 10; the variant including the R3C+T36C+N28G substitution of SEQ ID NO: 1 may be encoded by a polynucleotide represented by SEQ ID NO: 12; the variant including the R3C+T36C+N52P+N28G substitution of SEQ ID NO: 1 may be encoded by a polynucleotide represented by SEQ ID NO: 14; the variant including the S5C+S34C+N52P substitution of SEQ ID NO: 1 may be encoded by a polynucleotide represented by SEQ ID NO: 16; the variant including the S5C+S34C+N28G substitution of SEQ ID NO: 1 may be encoded by a polynucleotide represented by SEQ ID NO: 18; the variant including the S5C+S34C+N52P+N28G substitution of SEQ ID NO: 1 may be encoded by a polynucleotide represented by SEQ ID NO: 20; the variant including the F20C+A41+N52P substitution of SEQ ID NO: 1 may be encoded by a polynucleotide represented by SEQ ID NO: 22; the variant including the F20C+A41C+N28G substitution of SEQ ID NO: 1 may be encoded by a polynucleotide represented by SEQ ID NO: 24; and the variant including the F20C+A41C+N52P+N28G substitution of SEQ ID NO: 1 may be encoded by a polynucleotide represented by SEQ ID NO: 26.

In the variant provided in the present disclosure, one or more of any selectable or detectable properties or attributes of a polypeptide may be altered as compared to other xylanases, e.g., the wild-type xylanase, parent xylanase, other xylanase variants, etc.

The properties or attributes may include, but are not limited to oxidative stability, substrate specificity, catalytic activity, thermal stability, alkaline stability, pH activity profile, resistance to proteolytic degradation, $k_M$, $k_{cat}$, $k_{cat}/k_M$ ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and/or ability to treat diseases, etc.

In one embodiment, the variant provided in the present disclosure may have increased thermal tolerance and/or thermal stability compared to the parent sequence.

As used herein, the "enzymatic activity" exhibits at least one catalytic activity. Specifically, it may be the conversion efficiency of an enzyme mainly expressed as $k_{cat}/k_M$, but is not limited thereto.

When the enzyme is completely saturated with substrates, $k_{cat}$ means the rate constant (catalytic constant) that converts substrates into products in unit time by one enzyme, and is also referred to as a turnover number. $k_M$ is the substrate concentration when the reaction rate is at half the maximum value (Vmax).

Examples of the ways to express enzymatic activity include specific activity (umol of converted substrate×mg$^{-1}$×min$^{-1}$) or volumetric activity (umol of converted substrate×mL$^{-1}$×min$^{-1}$), etc.

However, defining the enzymatic activity is not limited to the contents described above, and the enzymatic activity can be defined and evaluated based on the information disclosed in the following literatures: Irwin H. Segel, Enzyme kinetics, John Wiley & Sons, 1979; A. G. Marangoni, Enzyme kinetics, Wiley-Interscience, 2003; A. Fersht, Enzyme structure and mechanisms, John Wiley & Sons, 1981; Structure and Mechanism in Protein Science: A guide to enzyme catalysis and protein folding, Alan Fersht, W. H. Freeman, 1999; Fundamentals of Enzyme Kinetics, Athel Cornish-Bowden, Wiley-Blackwell 2012 and Voet et al., "Biochemie" [Biochemistry], 1992, VCH-Verlag, Chapter 13, pages 331-332 with respect to enzymatic activity, etc.

In one embodiment, the variant provided in the present disclosure may have an increased enzymatic activity by about 100%, about 110%, about 120%, about 130%, about 140%, about 150%, about 160%, about 170%, about 180%, about 190%, or about 200% or more as compared to the parent enzyme.

In another embodiment, the variant provided in the present disclosure may have a decreased enzymatic activity by about 99%, about 95%, about 90%, about 80%, about 70%, about 60%, about 50%, about 40%, or about 20% or less as compared to the parent enzyme.

As used herein, the term "specific activity" is the activity of an enzyme per unit weight of proteins, and can be expressed as unit/mg. The quantification of proteins can be performed using, for example, SDS-PAGE or Bradford assay.

Enzyme stability means that enzyme activity is maintained during storage or reaction time. In order to measure such changes in stability, the initial enzyme activity can be measured and compared under defined conditions at time zero (100%) and after a certain period of time (x %), and thus, the level at which the enzyme activity is lost or enzyme stability can be expressed.

Factors that affect enzyme activity include, for example, pH, heat, the presence of other substances (e.g., oxidizing agents, chelating agents), etc.

As used herein, the term "pH stability" means the ability of a protein to function in a specific pH range. In one embodiment, the variant provided in the present disclosure may have activity at about pH 4.0 to about pH 12.0, but is not limited thereto.

When a protein maintains its function in a specific pH range, it can be defined as having "pH stability", and can also be defined as having "acid resistance", "alkali resistance", etc., according to the pH range.

As used herein, the term "thermal stability" means the ability of a protein to function in a specific temperature range. In one embodiment, the variant provided in the present disclosure may have activity in the range of about 20° C. to about 120° C., and specifically may have activity in the range of about 60° C. to about 100° C., but is not limited thereto.

As used herein, the term "thermal tolerance" means the ability of a protein to function after exposure to a specific temperature, e.g., high heat or cryogenic temperature. For example, proteins that are thermotolerant may not function at a temperature they are exposed to, but may become functional when returned to an optimal temperature environment.

An increase in stability may include maintaining high enzymatic activity; increasing the range of pH, temperature and/or time, etc., at which a protein maintains its function, by comparing to other enzymes, e.g., a wild-type enzyme, parent enzyme and/or other variants.

A decrease in stability may include maintaining low enzymatic activity; decreasing the range of pH, temperature and/or time, etc., at which a protein maintains its function, by comparing to other enzymes, e.g., a wild-type enzyme, parent enzyme and/or other variants.

As used herein, the term "substrate specificity" means the ability of an enzyme to identify a substrate and molecules that compete with the substrate. Substrate specificity can be determined by measuring the activity of an enzyme for different substrates. In one embodiment, the change in substrate specificity may be a change in the direction of increasing specificity for a substrate capable of producing a desired product. In another embodiment, the change in substrate specificity may be a change in a direction of decreasing specificity for a substrate capable of producing a desired product.

The altered properties of the variant provided in the present disclosure may be suitable or improved activity for application in various industrial fields, including feed, baking, pulp bleaching, etc.

The polynucleotide encoding the variant of the present disclosure may include the coding sequence of the above-described variant. The polynucleotide may undergo various modifications in the coding region within the scope that does not change the amino acid sequence of the polypeptide, due to codon degeneracy or in consideration of the codons preferred in an organism in which the polypeptide is to be expressed.

Additionally, the polynucleotide of the present disclosure may include a probe that may be prepared from a known gene sequence, for example, any sequence encoding the variant of the present disclosure by hybridizing with a sequence complementary to all or part of the nucleotide sequence described above under stringent conditions without limitation.

The "stringent conditions" refers to conditions under which specific hybridization between polynucleotides is allowed. Such conditions are specifically described in the literature (e.g., J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York).

For example, the stringent conditions may include conditions under which polynucleotides having a high homology or identity of 40% or more, specifically 90% or more, more specifically 95% or more, 96% or more, 97% or more, 98% or more, and even more specifically 99% or more are hybridized with each other and polynucleotides having a homology or identity lower than the above homologies or identities are not hybridized with each other, or washing conditions of the conventional Southern hybridization, that is, washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1×SSC, 0.1% SDS.

Hybridization requires that two nucleic acids contain complementary sequences, although mismatches between bases are possible depending on the stringency of the hybridization. The term "complementary" is used to describe the relationship between nucleotide bases that can hybridize with each other. For example, with respect to DNA, adenine is complementary to thymine, and cytosine is complementary to guanine. Therefore, the polynucleotide of the present disclosure may include isolated nucleotide fragments complementary to the entire sequence as well as nucleic acid sequences substantially similar thereto.

Specifically, polynucleotides having a homology or identity with the polynucleotide of the present disclosure may be detected using the hybridization conditions including a hybridization step at a $T_m$ value of 55° C. under the above-described conditions. Further, the $T_m$ value may be 60° C., 63° C., or 65° C., but is not limited thereto, and may be appropriately adjusted by those skilled in the art depending on the purpose thereof.

The appropriate stringency for hybridizing the polynucleotides depends on the length of the polynucleotides and the degree of complementation, and these variables are well known in the art (see, Sambrook et al., supra, 9.50-9.51, 11.7-11.8).

For example, the "high stringency" may occur at about 5 to 10° C. below the $T_m$ of the probe; the "medium stringency" may occur at about 10 to 20° C. below the $T_m$ of the probe; and the "low stringency" may occur at about 20 to 25° C. below the $T_m$, but the stringency is not limited thereto.

In one example, the "low stringency condition" may mean, for probes of at least about 100 nucleotides in length, prehybridization and hybridization at 42° C. in 5×SSPE, 0.3% SDS, 200 micrograms/ml of sheared and denatured salmon sperm DNA, and 25% formamide, according to the standard Southern blotting procedures for 12 to 24 hours. The carrier material is finally washed two or three times each for 15 minutes in 2×SSC, 0.1 to 0.2% SDS at 50° C.

In one example, the "medium stringency condition" may mean, for probes of at least about 100 nucleotides in length, prehybridization and hybridization at 42° C. in 5×SSPE, 0.3% SDS, 200 micrograms/ml of sheared and denatured salmon sperm DNA, and 35% formamide, according to the standard Southern blotting procedures for 12 to 24 hours. The carrier material is finally washed two or three times each for 15 minutes in 2×SSC, 0.1 to 0.2% SDS at 55° C.

In one example, the "medium-high stringency condition" may mean, for probes of at least about 100 nucleotides in length, prehybridization and hybridization at 42° C. in 5×SSPE, 0.3% SDS, 200 micrograms/ml of sheared and denatured salmon sperm DNA, and 35% formamide, according to the standard Southern blotting procedures for 12 to 24 hours. The carrier material is finally washed two or three times each for 15 minutes in 2×SSC, 0.1 to 0.2% SDS at 60° C.

In one example, the "high stringency condition" may mean, for probes of at least about 100 nucleotides in length, prehybridization and hybridization at 42° C. in 5×SSPE, 0.3% SDS, 200 micrograms/ml of sheared and denatured salmon sperm DNA, and 35% formamide, according to the standard Southern blotting procedures for 12 to 24 hours. The carrier material is finally washed two or three times each for 15 minutes in 2×SSC, 0.1 to 0.2% SDS at 65° C.

The nucleic acid construct provided in the present disclosure may include a polynucleotide encoding the variant provided herein, operably linked to one or more regulatory sequences that direct the expression of the coding sequence in an appropriate host cell under conditions suitable for the regulatory sequences.

The polynucleotides can be engineered in various ways to allow the expression of variants. Depending on the expression vector, it may be desirable or necessary to manipulate the polynucleotides prior to insertion into the vector. Such manipulations may be performed using methods known in the art.

The "vector" provided in the present disclosure refers to a DNA construct containing the nucleotide sequence of a polynucleotide encoding the variant operably linked to a suitable expression regulatory region (expression regulatory sequence) so as to be able to express the variant of the present disclosure in a suitable host cell. The expression regulatory region may include a promoter capable of initiating transcription, any operator sequence for regulating transcription, a sequence encoding a suitable mRNA ribosome-binding site, and a sequence for regulating termination of transcription and translation. Once transformed into a suitable host cell, the vector may replicate or function independently from the host genome, or may integrate into genome thereof.

The vector that can be used in the present disclosure is not particularly limited, and any vector known in the art may be used. Examples of the vectors typically used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, and Charon21A, etc. may be used; and as a plasmid vector, those based on pBR, pUC, pBluescriptII, pGEM, pTZ, pCL and pET, etc. may be used. Specifically, pDZ, pACYC177, pACYC184, pCL, pECCG117, pUC19, pBR322, pMW118, pCC1 BAC vector, etc. may be used.

In one example, a polynucleotide encoding the variant provided in the present disclosure may be inserted into the chromosome through a vector for intracellular chromosomal insertion. The insertion of the polynucleotide into the chromosome may be performed by any method known in the art, for example, by homologous recombination, but is not limited thereto. The vector may further include a selection marker to confirm the insertion into the chromosome. The selection marker is for selecting the cells transformed with the vector, that is, for confirming whether the target nucleic acid molecule has been inserted, and markers that provide selectable phenotypes, such as drug resistance, auxotrophy, resistance to cell toxic agents, or expression of surface polypeptides, may be used. Only cells expressing the selection marker are able to survive or show different phenotypes under the environment treated with the selective agent, and thus the transformed cells may be selected.

Any host cell may be included in the host cell of the present disclosure as long as it can express the variant of the present disclosure without limitation.

The host cell of the present disclosure may include the above-described variant, a polynucleotide encoding the variant, a nucleic acid construct and/or vector containing the same.

The nucleic acid construct or vector may be integrated into the chromosome as described earlier, or may remain as a self-replicating extrachromosomal vector.

The host cell of the present disclosure encompasses any progeny of a parent cell that is not identical to the parent cell due to mutations that occur during replication.

The host cell may be any cell useful in the recombinant production of a variant, e.g., a prokaryote or a eukaryote.

The prokaryotic host cell may be any Gram-positive or Gram-negative bacterium.

The Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*.

The Gram-negative bacteria include, but are not limited to, *Campylobacter, E. coli, Flavobacterium, Fusobacterium, Helicobacter, Ilyobacter, Neisseria, Pseudomonas, Salmonella, Vibrio* (e.g., *Vibrio natriegens*), and *Ureaplasma*.

In one embodiment, the bacterial host cell may be a host cell belonging to the genus *Bacillus*, specifically including *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells, but is not limited thereto.

In one embodiment, the bacterial host cell may be a host cell belonging to the genus *Streptococcus*, specifically including *Streptococcus equisimilis, Streptococcus pyogenes, Streptococcus uberis*, and *Streptococcus equi* subsp. *Zooepidemicus*, but is not limited thereto.

In one embodiment, the bacterial host cell may be a host cell belonging to the genus *Streptomyces*, specifically including *Streptomyces achromogenes, Streptomyces avermitilis, Streptomyces coelicolor, Streptomyces griseus*, and *Streptomyces lividans*, but is not limited thereto.

In one embodiment, the bacterial host cell may be a host cell belonging to the genus *Corynebacterium*, and may be *Corynebacterium glutamicum, Corynebacterium crudilactis, Corynebacterium deserti, Corynebacterium efficiens, Corynebacterium callunae, Corynebacterium stationis, Corynebacterium singulare, Corynebacterium halotolerans, Corynebacterium striatum, Corynebacterium ammoniagenes, Corynebacterium pollutisoli, Corynebacterium imitans, Corynebacterium testudinoris*, or *Corynebacterium flavescens*, but is not limited thereto.

In one embodiment, the host cell may be a microorganism belonging to the genus *Escherichia*, and may be *Escherichia coli, Escherichia albertii, Escherichia fergusonii, Escherichia hermannii, Escherichia vulneris*, or *Escherichia blattae*, but is not limited thereto.

The host cell may be a eukaryote, such as a mammalian, insect, plant, or fungal cell.

The host cell may be a fungal cell. As used herein, the "fungi" include Ascomycota, Basidiomycota, Chytridiomycota, and Zygomycota as well as the Oomycota and all mitosporic fungi.

The fungal host cell may be a yeast cell. As used herein, the "yeast" includes ascosporogenous yeast (Endomycetales), basidiosporogenous yeast, and yeast belonging to the Fungi imperfecti (Blastomycetes). However, the classification of yeasts may change, and can be defined as described in Biology and Activities of Yeast (Skinner, Passmore, and Davenport, editors, Soc. App. Bacteriol. Symposium Series No. 9, 1980).

The yeast host cell may be a *Candida, Hansenula, Kluyveromyces, Pichia, Komagataella, Saccharomyces, Schizosaccharomyces*, or *Yarrowia* cell, such as *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Komagataella phaffii*, or *Yarrowia lipolytica*.

The fungal host cell may be a filamentous fungal cell. As used herein, the "filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth by fungi is by hyphal elongation, and carbon catabolism is obligately aerobic. In contrast, vegetative growth by yeasts such as *Saccharomyces cerevisiae* is by budding of a unicellular thallus, and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be *Aspergillus awamori, Aspergillus foetidus, Aspergillus fumigatus, Aspergillus japonicus, Aspergillus nidulans,*

*Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride*, but is not limited thereto.

The method for preparing the variant of the present disclosure may include culturing a host cell.

As used herein, the term "cultivation" means that the host cell is grown under appropriately controlled environmental conditions. The cultivation process of the present disclosure may be performed in a suitable culture medium and culture conditions known in the art. Such a cultivation process may be easily adjusted for use by those skilled in the art according to the strain to be selected. Specifically, the cultivation may be a batch culture, a continuous culture, and a fed-batch culture, but is not limited thereto.

As used herein, the term "medium" refers to a mixture of materials which contains nutrient materials required for the cultivation of the host cell as a main ingredient, and it supplies nutrient materials and growth factors, along with water that is essential for survival and growth. Specifically, the medium and other culture conditions used for culturing the host cell of the present disclosure may be any medium used for conventional cultivation of host cells without any particular limitation. However, the host cell of the present disclosure may be cultured under aerobic conditions in a conventional medium containing an appropriate carbon source, nitrogen source, phosphorus source, inorganic compound, amino acid, and/or vitamin, while adjusting temperature, pH, etc.

In the present disclosure, the carbon source may include carbohydrates, such as glucose, saccharose, lactose, fructose, sucrose, maltose, etc.; sugar alcohols, such as mannitol, sorbitol, etc.; organic acids, such as pyruvic acid, lactic acid, citric acid, etc.; amino acids, such as glutamic acid, methionine, lysine, etc. Additionally, the carbon source may include natural organic nutrients such as starch hydrolysate, molasses, blackstrap molasses, rice bran, cassava, sugar cane molasses, and corn steep liquor, etc. Specifically, carbohydrates such as glucose and sterilized pretreated molasses (i.e., molasses converted to reducing sugar) may be used, and in addition, various other carbon sources in an appropriate amount may be used without limitation. These carbon sources may be used alone or in a combination of two or more kinds, but are not limited thereto.

The nitrogen source may include inorganic nitrogen sources, such as ammonia, ammonium sulfate, ammonium chloride, ammonium acetate, ammonium phosphate, ammonium carbonate, ammonium nitrate, etc.; amino acids, such as glutamic acid, methionine, glutamine, etc.; and organic nitrogen sources, such as peptone, NZ-amine, meat extract, yeast extract, malt extract, corn steep liquor, casein hydrolysate, fish or decomposition product thereof, defatted soybean cake or decomposition product thereof, etc. These nitrogen sources may be used alone or in a combination of two or more kinds, but are not limited thereto.

The phosphorus source may include monopotassium phosphate, dipotassium phosphate, or corresponding sodium-containing salts, etc. Examples of the inorganic compounds may include sodium chloride, calcium chloride, iron chloride, magnesium sulfate, iron sulfate, manganese sulfate, calcium carbonate, etc. Additionally, amino acids, vitamins, and/or appropriate precursors may be included. These constituting ingredients or precursors may be added to a medium in a batch or continuous manner, but these phosphorus sources are not limited thereto.

Additionally, the pH of the medium may be adjusted by adding a compound such as ammonium hydroxide, potassium hydroxide, ammonia, phosphoric acid, sulfuric acid, etc. during the cultivation of the host cell in an appropriate manner. In addition, bubble formation may be prevented during the cultivation using an antifoaming agent such as fatty acid polyglycol ester. Further, oxygen gas or a gas containing oxygen may be injected to the medium order to maintain aerobic conditions of the medium; or nitrogen gas, hydrogen gas, or carbon dioxide may be injected to maintain anaerobic or microaerobic conditions, without the injection of gas, but the gas is not limited thereto.

The temperature during the cultivation of the present disclosure may be in the range from 20° C. to 55° C., specifically from 25° C. to 40° C., but is not limited thereto. The cultivation may be continued until the desired amount of a useful material is obtained, and may be specifically carried out for 24 to 196 hours, but is not limited thereto.

In one embodiment, the method for preparing the modified polypeptide having xylanase activity of the present disclosure may further include recovering the modified polypeptide having xylanase activity of the present disclosure expressed in the culturing step.

In another embodiment, the variant expressed in the culturing step may be recovered using methods known in the art to which the present disclosure pertains. For example, the variant may be recovered from a nutrient medium by conventional procedures including, but not limited to, collection, centrifugation, filtration, extraction, spray-drying, evaporation, or precipitation.

In the recovering step, the variant may be collected using the method of culturing the host cell of the present disclosure, for example, using a suitable method known in the art according to a batch culture, continuous culture, or fed-batch culture method. For example, methods such as centrifugation, filtration, treatment with a protein crystallizing precipitant (salting-out method), extraction, ultrasonic disruption, ultrafiltration, dialysis, various kinds of chromatographies such as molecular sieve chromatography (gel filtration), adsorption chromatography, ion exchange chromatography, affinity chromatography, etc., HPLC and a combination thereof may be used, and the variant can be recovered from the medium or the host cell using suitable methods known in the art.

In another embodiment, the variant expressed by the host cell in the culturing step may not be recovered. In the embodiment, the host cell expressing the variant may be used as a source of the variant.

The composition of the present disclosure may be used to degrade xylan-containing materials.

The compositions of the present disclosure may be used to convert xylan-containing materials into xylose and/or xylo-oligosaccharides.

The composition of the present disclosure may further include other components in addition to the variant provided in the present disclosure. The components added to the composition of the present disclosure may be appropriately selected by those skilled in the art.

In one embodiment, the composition of the present disclosure may further include any components suitable for conversion of xylan-containing materials to xylose and/or xylo-oligosaccharides.

In one embodiment, the composition of the present disclosure may further include any components suitable for application in various industrial fields such as animal feed, baking, biomass saccharification, pulp bleaching, etc.

Examples of materials that may be added include stabilizers, surfactants, builders, chelating agents, dispersants, enzymes, enzyme stabilizers, catalysts, activators, carriers, binders, lubricants, disintegrants, excipients, solubilizers, suspending agents, colorants, flavoring agents, buffers, preservatives, analgesics, solubilizers, isotonic agents, stabilizers, diluents, lubricants, preservatives, etc., but are not limited thereto.

In one embodiment, the composition provided in the present disclosure may further include a naturally occurring material or a non-naturally occurring material, in addition to the variant provided in the present disclosure.

In one embodiment, the composition provided in the present disclosure may further include additional enzymes commonly used in various industrial fields, including animal feed, baking, biomass saccharification, pulp bleaching, etc., in addition to the variant provided in the present disclosure.

For example, the additional enzymes may further include any one or more enzymes selected from the group consisting of beta-amylase, cellulase (e.g., beta-glucosidase, cellobiohydrolase and endoglucanase), glucoamylase, hemicellulsae (e.g., endo-xylanase, β-xylosidase, α-L-arabionofuranosidase, α-D-glucuronidase, feruloyl esterase, coumaroyl esterase, α-galactosidase, β-galactosidase, β-mannanase or β-mannosidase), isoamylase, isomerase, lipase, phytase, protease, pullulanase, and/or other enzymes useful in a commercial process in conjunction with alpha-amylase.

The xylanase variant of the present disclosure or the composition including the xylanase variant of the present disclosure may be used to degrade any xylan-containing materials.

As used herein, the xylan-containing material is any material that can be degraded by xylanase. In one example, the xylan-containing material may be hemicellulose. Specifically, the xylan-containing material may be a material selected from xylan, glucuronoxylan, arabinoxylan, glucomannan and xyloglucan. In one example, the xylan-containing material may be xylan, but is not limited thereto.

In one embodiment, the present disclosure provides a method for degrading (or break down) xylan-containing materials. This may also be referred to as solubilization of xylan and/or solubilization of pentosans.

In further embodiment of the present disclosure, the method relates to the degradation of polymers (e.g., break down) derived from the degradation of xylan.

The breakdown products (e.g., glucose) can be used as a feedstock for any fermentation process, such as in biofuel (e.g., bioethanol) production or in the production of other products such as biochemicals (e.g., bio-based isoprene).

Xylan can be degraded using the variant of the present disclosure, a host cell expressing the same, and/or a composition including the variant and/or the host cell. In addition to the variant of the present disclosure, cofactors, coenzymes, etc. may be added in combination in the hydrolysis step of xylan. The hydrolysis step of the substrate may be performed under optimal pH, temperature conditions, etc., and appropriate conditions can be selected by those skilled in the art.

The xylanase variant of the present invention may be used in any one of the following applications:

a) an additive in animal feedstuffs; and/or b) a feed supplement for animals; and/or c) breakdown of grain-based materials (e.g., this can be whole grain or part of grain).

In one embodiment, the xylanase variant of the present disclosure may be used in feedstuffs.

In one embodiment, the xylan-containing material may be a feedstuff or a feed component.

The feed composition of the present disclosure may refer to any natural or artificial diet, a single meal, etc., or a component of the single meal, which an animal eats, ingests and digests, or which is suitable for eating, ingestion and digestion, and the feed composition may be prepared in various forms known in the art.

In one embodiment, the xylanase variant of the present disclosure may be used for a food composition or the preparation thereof.

In one embodiment, the xylan-containing material may be a grain-based material (including whole or part of grains, or malted grains, e.g., malted barley).

In one embodiment, the xylan-containing material may be a cereal flour (e.g., wheat, oat, rye or barley flour).

In one embodiment the xylan-containing material may be a barley malt or mash, or malted barley or combinations thereof.

In one example, the food composition may be a fermented beverage including beer and wine.

In another example, the food composition may be bakery products, including loaves, rolls, buns, pizza, pretzels, tortillas, cakes, cookies, biscuits, and crackers, but is not limited thereto.

The xylanase variant of the present disclosure may be used for wheat gluten-starch separation.

After initial separation of the wheat bran and germ from the endosperm, fractionation of wheat endosperm flour into starch and gluten fractions may be employed to obtain high quality α-starch, β-starch byproducts and vital gluten.

In the method for separating a cereal flour (e.g., wheat flour) into starch and gluten fractions, the method includes mixing a cereal flour (e.g., wheat flour), water and the xylanase variant. The cereal flour, water and xylanase variant may be mixed simultaneously or sequentially. In some embodiments, the cereal flour (e.g., wheat flour) and water may be mixed before mixing with the xylanase variant.

When the xylanase variant of the present disclosure is applied for wheat gluten-starch separation, it results in higher α-starch yields and/or better-quality gluten (e.g., better-quality vital gluten).

In another embodiment, the xylanase variant of the present disclosure may be used for the degradation of grain-based materials and may be used as part of a biofuel (e.g., bioethanol) production process.

In one example, the xylanase variant of the present disclosure may improve the production of biofuels (e.g., bioethanol) and the use of grain-based materials in the biofuel industry.

In one example, the method may include mixing a biofuel with the xylanase variant prior to or during liquefaction, saccharification, fermentation, simultaneous saccharification and fermentation, post fermentation, or a combination thereof.

When the xylanase variant of the present disclosure is applied for a biofuel production process, the following advantages may be obtained: higher content of dry substance mash may be used in the process; higher solids content of final syrup may be obtained; higher heat transfer; lower energy requirement; reduced evaporator fouling; reduced cleaning costs; increased final fuel yields; improved quality of by-product; better separation between the solid and liquid part of stillage after distillation; or a combination thereof.

The xylanase variant of the present disclosure may be used for pulp bleaching.

For example, when the xylanase variant is treated while the pigmented lignin in the pulp is linked to crystalline cellulose via xylan, xylan can be degraded and the pigmented lignin can be released, thereby promoting pulp bleaching.

EXAMPLES

Hereinafter, the present disclosure will be described in more detail by way of Examples and Experimental Examples. However, these Examples and Experimental Examples are given for illustrative purposes only, and the scope of the present disclosure is not intended to be limited by these Examples and Experimental Examples.

Example 1: Preparation of Variants 1-1. Preparation of Template

In the genomic DNA of the *Orpinomyces* sp. PC-2 strain, the gene (SEQ ID NO: 2) of xylanase variant (hereinafter referred to as Op Xyn, SEQ ID NO: 1) was amplified and cloned into a pHCE vector (Takara), and then was used as a template.

1-2. Preparation of Point Variants

Sites for generating a single mutation in Op Xyn were selected, and variants were prepared via site direct mutagenesis (SDM) and site saturation mutagenesis (SSM) using the primers shown in Table 1 below (Table 1). In the mutation description of Table 1 below, the amino acids before mutation, mutation positions based on the amino acid sequence of SEQ ID NO: 1, and the amino acids after mutation are sequentially described.

TABLE 1

| Name of Variant | Mutation Description | SEQ ID NO: | | Primer (5' → 3') |
|---|---|---|---|---|
| SDM1 | R105D | 27 | Forward | TGGTTCCAGAACGATGGAGTGCAGG GC |
| | | 28 | Reverse | GTTCTGGAACCAGCCGTAG |
| SDM2 | R105N | 29 | Forward | TGGTTCCAGAACAACGGAGTGCAGG GC |
| | | 30 | Reverse | GTTCTGGAACCAGCCGTAG |
| SDM3 | S91N | 31 | Forward | AGACTGCCAGCGCAAACGGTAACAG C |
| | | 32 | Reverse | TGCGCTGGCAGTCTGCC |
| SDM4 | N52P | 33 | Forward | AGCGCAGCTGTCCCCCGGGGTAAC |
| | | 34 | Reverse | GACAGCTGCGCTCCACTC |
| SDM5 | S66G | 35 | Forward | CTGGATTTCGGCGGTACCAAGAAGG CC |
| | | 36 | Reverse | GCCGAAATCCAGACCGCG |
| SDM6 | S66N | 37 | Forward | CTGGATTTCGGCAACACCAAGAAGG CC |
| | | 38 | Reverse | GCCGAAATCCAGACCGCG |
| SDM7 | N28G | 39 | Forward | ATCTGGCTGGATGGCACCGGCGG |
| | | 40 | Reverse | ATCCAGCCAGATCTCG |
| SDM8 | S178I | 41 | Forward | ACCGTCATCGATCACTTC |
| | | 42 | Reverse | GTGATCGATGACGGTGAT |
| SDM9 | Y162W | 43 | Forward | AAGCAGTGGTTCAGCGTCCGC |
| | | 44 | Reverse | GCTGAACCACTGCTTGAAGGTCTC |
| SSM1 | S91X | 45 | Forward | AGACTGCCAGCGCANNKGGTAACAG C |
| | | 46 | Reverse | TGCGCTGGCAGTCTGCC |
| SSM2 | N52X | 47 | Forward | AGCGCAGCTGTCNNKCGGGGTAAC |
| | | 48 | Reverse | GACAGCTGCGCTCCACTC |
| SSM3 | N28X | 49 | Forward | ATCTGGCTGGATNNKACCGGCGGTA G |
| | | 50 | Reverse | ATCCAGCCAGATCTCG |
| SSM4 | G8X | 51 | Forward | TTGAGCGTCGGTNNKGGCCAGAACC |
| | | 52 | Reverse | ACCGACGCTCAACCTCTG |

Specifically, the xylanase variants were prepared by PCR using the template, primers, and a PCR premix (iNtRON, cat no. 25185). PCR was performed using Eppendorf Master-cycler Nexus GX2, and the reaction conditions are as follows:

Initial Denaturation—94° C., 2 min

Denaturation—94C, 20 sec

Annealing—50° C., 10 sec

Extension—72° C., 10 min (From denaturation to extension 30 cycle)

Final Extension—72C, 5 min

The resulting variants were ligated using an In-Fusion HD cloning kit (Takara, Cat. No. 639650), and then transformed into an *E. coli* Dh5α strain, followed by sequencing to confirm sequence mutation.

Example 2. Selection of Variants and Evaluation of Thermal Tolerance 2-1. Evaluation of Thermal Tolerance for Variants Induced by Site Direct Mutagenesis The *E. coli* Dh5α strains transformed with the SDM variants prepared in Example 1 and the Op Xyn gene were each inoculated into a sterilized LB medium (BD Difco), and cultured for 24 hours at 37° C. and 180 rpm, and then the cells were recovered by centrifugation. 20 ml of lysis buffer (50 mM Tris-HCl pH 8.0, 100 mM NaCl, 10 mM imidazole) was added to the recovered cells and redispersed, and then a crude enzyme solution was obtained through sonication and centrifugation. The crude enzyme solution was flowed through a Ni-NTA resin (Qiagen, Cat no. 30230) to be adsorbed, followed by sequentially flowing washing buffer (only 20 mM of imidazole in the lysis buffer composition) and elution buffer (only 250 mM of imidazole in the lysis buffer composition) to purify the enzyme, and the activity and thermal tolerance were evaluated using the purified enzyme.

The enzyme concentration was obtained by mixing 4 μl of the diluted enzyme solution+196 μl of Bradford solution (Quick Start™ Bradford 1× Dye Reagent, #5000205) and then measuring the absorbance at 595 nm.

The enzyme activity was measured by mixing 4 μl of 1 M pH 6.5 phosphate buffer with 96 μl of 1% xylan from beachwood (Megazyme, P-XYLNBE-10G), and then adding 100 μl of the diluted enzyme solution thereto, followed by carrying out the reaction at 37° C. for 15 minutes. 300 μl of a DNS solution was mixed with the reaction solution to stop the reaction, and the mixture was boiled for 7 minutes to allow color development, and then cooled in ice water. The absorbance of the solution mixed with 500 μl of distilled water was measured at 550 nm, and the activity was measured using a standard curve made of xylose (Sigma-Aldrich, X1500).

The method for preparing the DNS solution was as follows:

6.3 g of 3,5-dinitrosalicylic acid (samchun, D1267) was added to a beaker containing 500 ml of distilled water, and 21 g of sodium hydroxide (Daejung, 7571-4400) was added thereto at 50° C. After adding 300 ml of water and 182 g of potassium sodium tartrate tetrahydrate (Daejung, 6618-4400) to the mixture, 5 g of phenol (Sigma-Aldrich, P1037) and 5 g of sodium sulfite anhydrous (Daejung, 7634-4405) were added, and the mixture was stirred until dissolved and then cooled. Distilled water was added to the mixture to adjust the total volume to 1000 ml and filtered, and then stored in a brown bottle for 7 days or more before use.

In order to evaluate thermal tolerance, the purified enzyme was diluted to a concentration of 0.5 mg/ml and incubated in a water bath at 70° C. for 10 minutes, and then the residual activity was measured. Two mutans (SDM4/7) with improved thermal stability (residual activity) by more than 10-fold relative to the Op Xyn were selected.

TABLE 2

| Name of Variant | Position of Mutation | 70° C. Residual Activity (%) |
|---|---|---|
| Op Xyn | — | 2.9 |
| SDM1 | R105D | 2.5 |
| SDM2 | R105N | 3.4 |
| SDM3 | S91N | 6.8 |
| SDM4 | N52P | 48.0 |
| SDM5 | S66G | 3.9 |
| SDM6 | S66N | 3.3 |
| SDM7 | N28G | 65.9 |
| SDM8 | S171I | 13.8 |
| SDM9 | Y162W | 4.1 |

2-2. Evaluation of Thermal Tolerance for Variants Induced by Site Saturation Mutagenesis The *E. coli* Dh5α strains transformed with the SSM variants prepared in Example 1 and the Op Xyn gene were plated on an LB plate containing an antibiotic (Kanamycin), and then stationary cultured in a 37° C. incubator for 24 hours. The thus-obtained colonies were inoculated into a 96-well plate, in which 0.4 ml of LB medium was dispensed one by one, cultured for 24 hours at 37° C. and 750 rpm, and then centrifuged at 4000 rpm for 15 minutes to recover cells (Eppendorf Centrifuge 5810R). The recovered cells were treated with 100 μl of B-PER Bacterial Protein Extraction reagent (Thermo, #78248), incubated for 10 minutes, and then mixed with 300 μl of distilled water, and centrifuged at 4000 rpm for 15 minutes to obtain a crude enzyme solution. After heat-treating the crude enzyme solution in a water bath at 70° C. for 15 minutes, the xylanase activity was analyzed using absorbance on a scale down to 1/5 in a 96-well plate. Based on the residual absorbance of the Op Xyn, colonies having 150% or more were selected, and their nucleotide sequences were analyzed to confirm the variants. As a result, it was confirmed that the selected variants were N52P, N52A, and N52E in SSM2, and N28S, N28L, N28A, N28V, N28G, and N28W in SSM3.

After purifying each of the variants, the thermal stability of the purified enzymes was further evaluated (70° C. for 10 minutes). As a result, it was confirmed that the thermal stability of N52P, N52A, and N52E in SSM2 and N28A, N28G, and N28S in SSM3 was improved.

TABLE 3

| Name of Variant | Position of Mutation | 70° C. Residual Activity (%) |
|---|---|---|
| Op Xyn | — | 2.3 |
| SSM2 | N52P | 24.2 |
| (N52X) | N52A | 9.7 |
| | N52E | 5.4 |
| SSM3 | N28S | 6.5 |
| (N28X) | N28L | 1.4 |
| | N28A | 59.2 |
| | N28V | 1.4 |
| | N28G | 31.2 |
| | N28W | 2.1 |

Example 3: Introduction of Additional Disulfide Bond Mutations 3-1. Preparation of Disulfide Bond Variants Seven variants as shown in Table 4 below were prepared by selecting an amino acid pair site for generating a disulfide bond in Op Xyn and designing primers for mutating the corresponding amino acid sequences to cysteine. In the mutation description of Table 4 below, the amino acids before mutation, mutation positions based on the amino acid sequence of SEQ ID NO: 1, and the amino acids after mutation are sequentially described.

TABLE 4

| Name of Variant | Mutation Description | SEQ ID NO: | | Primer (5' → 3') |
|---|---|---|---|---|
| DS1 | R3C | 53 | Forward | GGCCAGTGTTTGAGCGTCGG |
| | | 54 | Reverse | GCTCAAACACTGGCCCATATGG |
| | T36C | 55 | Forward | AAGGGATGTACCTTCAAGGCTGAG |
| | | 56 | Reverse | ACCCAGACACATGGAACCGCTACC |
| DS2 | S5C | 57 | Forward | AGGTTGTGTGTCGGTGGTGG |
| | | 58 | Reverse | ACCGACACACAACCTCTGGCC |
| | S34C | 59 | Forward | AGCGGTTGTATGACCCTGGGTAAG |
| | | 60 | Reverse | GGTCATACAACCGCTACCGCC |
| DS3 | A128C | 61 | Forward | CCGGATTGTCAGGGAAAGATGGTCAC |
| | | 62 | Reverse | TCCCTGACAATCCGGGACCCAG |
| | F143C | 63 | Forward | AAGATCTGTCAGATGGATCACACTGG |
| | | 64 | Reverse | CATCTGACAGATCTTGTACTGGGCG |
| DS4 | S66C | 65 | Forward | TTCGGCTGTACCAAGAAGGCC |
| | | 66 | Reverse | CTTGGTACAGCCGAAATCCAGACC |
| | N193C | 67 | Forward | ATCGGCTGTCTCTACGAGGTCGCA |
| | | 68 | Reverse | GTAGAGACAGCCGATGCCCC |
| DS5 | F20C | 69 | Forward | GATGGCTGTAGCTACGAGATCTGG |
| | | 70 | Reverse | GTAGCTACAGCCATCGAAGACGC |
| | A41C | 71 | Forward | AAGGGATGTACCTTCAAGGCTGAG |
| | | 72 | Reverse | GAAGGTACATCCCTTACCCAGGG |
| DS6 | T71C | 73 | Forward | AAGGCCTGTGCTTACGAGTACATCG |
| | | 74 | Reverse | GTAAGCACAGGCCTTCTTGGTGG |
| | I191C | 75 | Forward | TGGGGCTGTGGCAACCTCTACG |
| | | 76 | Reverse | GTTGCCACAGCCCCAGCCC |
| DS7 | L62C | 77 | Forward | CGCGGTTGTGATTTCGGCTCCAC |
| | | 78 | Reverse | GAAATCACAACCGCGTCGGGC |
| | V217C | 79 | Forward | CTGGATTGTTACACCACCAAGCAGG |
| | | 80 | Reverse | GGTGTAACAATCCAGCTTGGTGACG |

Specifically, the disulfide bond variants were prepared by PCR using the template, primers, and a PCR premix (iNtRON, cat no. 25185). PCR was performed using Eppendorf Mastercycler Nexus GX2, and the reaction conditions are as follows:

Initial Denaturation—9400, 2 min

Denaturation—94C, 20 sec

Annealing—50°, 10 sec

Extension—72° C., 10 min (From denaturation to extension 30 cycle)

Final Extension—72C, 5 min

The resulting seven variants were ligated using an In-Fusion HD cloning kit (Takara, Cat. No. 639650), and then transformed into an *E. coli* Dh5α strain, followed by sequencing to confirm sequence mutation.

3-2. Selection of Variants with Improved Thermal Tolerance and Confirmation of Thermal Tolerance Effects The *E. coli* Dh5α strains transformed with the variants prepared in Example 3-1 and the Op Xyn gene were each inoculated into a sterilized LB medium (BD Difco), and cultured for 24 hours at 37° C. and 180 rpm, and then the cells were recovered by centrifugation. 20 ml of lysis buffer (50 mM Tris-HCl pH 8.0, 100 mM NaCl, 10 mM imidazole) was added to the recovered cells and redispersed, and then, a crude enzyme solution was obtained through sonication and centrifugation. The crude enzyme solution was flowed through Ni-NTA resin (Qiagen, Cat no. 30230) to be adsorbed, followed by sequentially flowing washing buffer (only 20 mM of imidazole in the dissolution buffer composition) and elution buffer (only 250 mM of imidazole in the dissolution buffer composition) to purify the enzyme, and the activity and thermal tolerance were evaluated using the purified enzyme in the same manner as in Example 2.

The enzyme concentration was obtained by mixing 4 μl of the diluted enzyme solution+196 μl of Bradford solution (Quick Start™ Bradford 1× Dye Reagent, #5000205) and then measuring the absorbance at 595 nm.

The enzyme activity was measured by mixing 4 μl of 1 M pH 6.5 phosphate buffer with 96 μl of 1% xylan from beachwood (Megazyme, P-XYLNBE-10G), and then adding 100 μl of the diluted enzyme solution thereto, followed by carrying out the reaction at 37° C. for 15 minutes. 300 μl of a DNS solution was mixed with the reaction solution to stop the reaction, and the color was developed by boiling for 7 minutes and then cooled in ice water. The absorbance of the solution mixed with 500 μl of distilled water was measured at 550 nm, and the activity was measured using a standard curve made of xylose (Sigma-Aldrich, X1500).

The method for preparing the DNS solution was as follows:

6.3 g of 3,5-dinitrosalicylic acid (samchun, D1267) was added to a beaker containing 500 ml of distilled water, and the temperature of the mixture was adjusted to 50° C., and then 21 g of sodium hydroxide (Daejung, 7571-4400) was added thereto. After adding 300 ml of water and 182 g of potassium sodium tartrate tetrahydrate (Daejung, 6618-4400) to the mixture, 5 g of phenol (Sigma-Aldrich, P1037) and 5 g of sodium sulfite anhydrous (Daejung, 7634-4405) were added, and the mixture was stirred until dissolved and then cooled. Distilled water was added to the mixture to adjust the total volume to 1000 ml and filtered, and then stored in a brown bottle for 7 days or more before use.

In order to evaluate thermal tolerance, the purified enzyme was diluted to a concentration of 0.5 mg/ml and incubated in a water bath at 70° C. for 10 minutes, and then the residual activity was measured.

TABLE 5

| Name of Variant | Activity (U/mg) | Relative Activity Relative to Op Xyn (%) | 70° C. Residual Activity (%) |
|---|---|---|---|
| Op Xyn | 4363 | 100 | 1.8 |
| DS1 | 13877 | 318 | 80.8 |
| DS2 | 2566 | 59 | 64.7 |
| DS3 | 731 | 17 | 3.7 |
| DS4 | 1290 | 30 | 3.8 |
| DS5 | 4302 | 99 | 17.0 |
| DS6 | 1079 | 25 | 3.8 |
| DS7 | 264 | 6 | 11.1 |

As a result, when the enzyme activity was measured as a ratio, three variants (DS1, DS2, and DS5) with improved thermal tolerance (residual activity) by more than 5 times while having the enzyme activity (specific activity) in the range of 50 to 300% relative to the Op Xyn were selected.

The changes in the residual activity of the selected variant strains according to the incubation time at 70° C. of DS1, DS2, and DS5 were additionally confirmed and are shown in FIG. 4. As a result, it was confirmed that there was hardly no change in the residual activities of DS1, DS2, and DS5 even when the treatment time was increased.

3-3. Evaluation of Thermal Stability of Variants Introduced with Additional Disulfide Bond Mutation The three mutations DS1(R3C+T36C) DS2(S5C+S34C), and DS5(F20C+A41C) confirmed in Example 3-2 were additionally introduced into the mutations identified in Examples 1 and 2. After preparing the purified enzyme as described above, the relative activity relative to Op Xyn, and the thermal stability at 70° C. and 80° C. were measured (FIGS. 1-5). As a result, it can be confirmed that the thermal stability was improved as the point mutations discovered in Examples 1 and 2 were added to the disulfide bond variants.

TABLE 6

| Name of Variant | Position of Mutation | Relative Activity Relative to Op Xyn (%) | | Residual Activity (%) | |
|---|---|---|---|---|---|
| | | U/mg | % | 70° C. 10 min | 80° C. 5 min |
| Op Xyn | — | 4363.0 | 100.0 | 1.8 | 0.3 |
| DS1 | R3C + T36C | 13877.2 | 318.1 | 80.8 | 1.8 |
| DS1 + SDM4 | R3C + T36C + N52P | 14632.6 | 335.4 | 101.2 | 23.4 |
| DS1 + SDM7 | R3C + T36C + N28G | 8850.3 | 202.8 | 104.8 | 21.4 |
| DS1 + SDM4 + 7 | R3C + T36C + N28G + N52P | 9303.6 | 213.2 | 108.1 | 72.7 |
| DS2 | S5C + S34C | 2565.6 | 58.8 | 64.7 | 7.9 |
| DS2 + SDM4 | S5C + S34C + N52P | 2222.2 | 50.9 | 95.6 | 69.4 |
| DS2 + SDM7 | S5C + S34C + N28G | 1968.4 | 45.1 | 97.0 | 46.5 |
| DS2 + SDM4 + 7 | S5C + S34C + N28G + N52P | 1253.0 | 28.7 | 88.2 | 81.8 |
| DS5 | F20C + A41C | 4301.9 | 98.6 | 17.0 | |
| DS5 + SDM4 | F20C + A41C + N52P | 7470.0 | 171.2 | 23.0 | |
| DS5 + SDM7 | F20C + A41C + N28G | 3585.9 | 82.2 | 25.1 | |
| DS5 + SDM4 + 7 | F20C + A41C + N28G + N52P | 6356.1 | 145.7 | 22.1 | |

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

---

The invention claimed is:

1. A modified polypeptide comprising the amino acid sequence of SEQ ID NO: 1 and having one or more substitutions selected from the group below:

N28A;
N28G;
N28S;
N52P;
N52A;
N52E;
N28A+N52P;
N28A+N52A;
N28A+N52E;
N28G+N52P;
N28G+N52A;
N28G+N52E;
N28S+N52P;
N28S+N52A;
N28S+N52E; and
wherein the position number is a position corresponding to the position of the polypeptide of SEQ ID NO: 1.

2. The modified polypeptide of claim 1, encoded by the polynucleotide sequence of SEQ ID NO: 10, SEQ ID NO: 12, SEQ ID NO: 14, SEQ ID NO: 16,SEQ ID NO: 18, SEQ ID NO: 20, SEQ ID NO: 22, SEQ ID NO: 24, or SEQ ID NO: 26.

3. The modified polypeptide of claim 1, wherein the modified polypeptide further comprises substitutions of amino acids at positions selected from i) to vii) below with cysteine:

i) 3+36;
ii) 5+34;
iii) 20+41;
iv) 3+36+5+34;
v) 3+36+20+41;
vi) 5+34+20+41; and
vii) 3+36+5+34+20+41;
wherein the position number is a position corresponding to the position of the polypeptide of SEQ ID NO: 1.

4. The modified polypeptide of claim 3, wherein the modified polypeptide comprises substitutions of two or more amino acids at positions 3, 5, 20, 34,36, and 41 with cysteine, and forms a disulfide bridge between the two substituted amino acids.

5. The modified polypeptide of claim 1, wherein the modified polypeptide further comprises substitution of an amino acid pair at positions 3 and 36 with cysteine; substitution of an amino acid pair at positions 5 and 34 with cysteine; or substitution of an amino acid pair at positions 20 and 41 with cysteine; and modification of the amino acid pairs to form a disulfide bridge.

6. The modified polypeptide of claim 1, wherein the modified polypeptide has increased thermal tolerance or thermal stability compared to a polypeptide composed of the amino acid sequence of SEQ ID NO: 1.

7. A method for producing xylo-oligosaccharides or xylose, comprising: (a) contacting a xylan-containing material to the modified polypeptide of claim 1, (b) contacting a xylan-containing material to an isolated host cell expressing the modified polypeptide of claim 1, or (c) contacting a xylan-containing material to a composition comprising the modified polypeptide of claim 1.

8. A method of degrading xylan, comprising: (a) contacting a xylan-containing material with the modified polypeptide of claim 1, (b) contacting a xylan-containing material with an isolated host cell expressing the modified polypeptide of claim 1, or (c) contacting a xylan-containing material to a composition comprising the modified polypeptide of claim 1.

9. A polynucleotide encoding the modified polypeptide of claim 1.

10. An isolated transformed host cell comprising the modified polypeptide of claim 1 or the polynucleotide encoding the modified polypeptide of claim 1.

11. A method for preparing a modified polypeptide having xylanase activity, comprising culturing the isolated transformed host cell of claim 10.

*     *     *     *     *

SEQUENCE LISTING

<160> NUMBER OF SEQ ID NOS: 80

<210> SEQ ID NO 1
<211> LENGTH: 227
<212> TYPE: PRT
<213> ORGANISM: Artificial Sequence
<220> FEATURE:
<223> OTHER INFORMATION: Op Xyn

<400> SEQUENCE: 1

Gly Gln Arg Leu Ser Val Gly Gly Gly Gln Asn Gln His Lys Gly Val
1               5                   10                  15

Phe Asp Gly Phe Ser Tyr Glu Ile Trp Leu Asp Asn Thr Gly Gly Ser
                20                  25                  30

Gly Ser Met Thr Leu Gly Lys Gly Ala Thr Phe Lys Ala Glu Trp Ser
            35                  40                  45

Ala Ala Val Asn Arg Gly Asn Phe Leu Ala Arg Arg Gly Leu Asp Phe
        50                  55                  60

Gly Ser Thr Lys Lys Ala Thr Ala Tyr Glu Tyr Ile Gly Leu Asp Tyr
65                  70                  75                  80

Glu Ala Ser Tyr Arg Gln Thr Ala Ser Ala Ser Gly Asn Ser Arg Leu
                85                  90                  95

Cys Val Tyr Gly Trp Phe Gln Asn Arg Gly Val Gln Gly Val Pro Leu
            100                 105                 110

Val Glu Tyr Tyr Ile Ile Glu Asp Trp Val Asp Trp Val Pro Asp Ala
            115                 120                 125

Gln Gly Lys Met Val Thr Ile Asp Gly Ala Gln Tyr Lys Ile Phe Gln
        130                 135                 140

Met Asp His Thr Gly Pro Thr Ile Asn Gly Gly Asn Glu Thr Phe Lys
145                 150                 155                 160

Gln Tyr Phe Ser Val Arg Gln Gln Lys Arg Thr Ser Gly His Ile Thr
                165                 170                 175

Val Ser Asp His Phe Lys Ala Trp Ala Asn Gln Gly Trp Gly Ile Gly
            180                 185                 190

Asn Leu Tyr Glu Val Thr Leu Asn Ala Glu Gly Trp Gln Ser Ser Gly
            195                 200                 205

Val Ala Asp Val Thr Lys Leu Asp Val Tyr Thr Thr Lys Gln Gly Ser
        210                 215                 220

Ala Pro Arg
225

<210> SEQ ID NO 2
<211> LENGTH: 684
<212> TYPE: DNA
<213> ORGANISM: Artificial Sequence
<220> FEATURE:
<223> OTHER INFORMATION: Op Xyn NT

<400> SEQUENCE: 2
ggccagaggt tgagcgtcgg tggtggccag aaccagcaca agggcgtctt cgatggcttc        60
agctacgaga tctggctgga taacaccggc ggtagcggtt ccatgaccct gggtaaggga       120

-continued

```
gctaccttca aggctgagtg gagcgcagct gtcaaccggg gtaacttcct ggcccgacgc        180
ggtctggatt tcggctccac caagaaggcc accgcttacg agtacatcgg cctggattac        240
gaggcaagct acaggcagac tgccagcgca agcggtaaca gccgcctctg cgtctacggc        300
tggttccaga accgggggagt gcagggcgtc ccctggtcg agtactacat catcgaggat        360
tgggtcgact gggtcccgga tgcgcaggga agatggtca ccatcgatgg cgcccagtac        420
aagatcttcc agatggatca cactggcccg accatcaacg gcggtaacga gaccttcaag        480
cagtacttca gcgtccgcca gcagaagcgc actagcggcc acatcaccgt cagcgatcac        540
ttcaaggcgt gggccaacca gggctggggc atcggcaacc tctacgaggt cacactgaac        600
gcagagggtt ggcagagcag tggtgtcgcc gacgtcacca agctggatgt ctacaccacc        660
aagcagggtt cggcccctcg ttag                                               684
```

<210> SEQ ID NO 3
<211> LENGTH: 227
<212> TYPE: PRT
<213> ORGANISM: Artificial Sequence
<220> FEATURE:
<223> OTHER INFORMATION: DS1(R3C+T36C)

<400> SEQUENCE: 3

```
Gly Gln Cys Leu Ser Val Gly Gly Gln Asn Gln His Lys Gly Val
1               5                   10                  15

Phe Asp Gly Phe Ser Tyr Glu Ile Trp Leu Asp Asn Thr Gly Gly Ser
            20                  25                  30

Gly Ser Met Cys Leu Gly Lys Gly Ala Thr Phe Lys Ala Glu Trp Ser
            35                  40                  45

Ala Ala Val Asn Arg Gly Asn Phe Leu Ala Arg Arg Gly Leu Asp Phe
        50                  55                  60

Gly Ser Thr Lys Lys Ala Thr Ala Tyr Glu Tyr Ile Gly Leu Asp Tyr
65                  70                  75                  80

Glu Ala Ser Tyr Arg Gln Thr Ala Ser Ala Ser Gly Asn Ser Arg Leu
                85                  90                  95

Cys Val Tyr Gly Trp Phe Gln Asn Arg Gly Val Gln Gly Val Pro Leu
            100                 105                 110

Val Glu Tyr Tyr Ile Ile Glu Asp Trp Val Asp Trp Val Pro Asp Ala
            115                 120                 125

Gln Gly Lys Met Val Thr Ile Asp Gly Ala Gln Tyr Lys Ile Phe Gln
        130                 135                 140

Met Asp His Thr Gly Pro Thr Ile Asn Gly Gly Asn Glu Thr Phe Lys
145                 150                 155                 160

Gln Tyr Phe Ser Val Arg Gln Gln Lys Arg Thr Ser Gly His Ile Thr
                165                 170                 175

Val Ser Asp His Phe Lys Ala Trp Ala Asn Gln Gly Trp Gly Ile Gly
            180                 185                 190

Asn Leu Tyr Glu Val Thr Leu Asn Ala Glu Gly Trp Gln Ser Ser Gly
            195                 200                 205

Val Ala Asp Val Thr Lys Leu Asp Val Tyr Thr Thr Lys Gln Gly Ser
        210                 215                 220

Ala Pro Arg
225
```

<210> SEQ ID NO 4
<211> LENGTH: 684

<212> TYPE: DNA
<213> ORGANISM: Artificial Sequence
<220> FEATURE:
<223> OTHER INFORMATION: DS1(R3C+T36C) nt

<400> SEQUENCE: 4

```
ggccagtgtt tgagcgtcgg tggtggccag aaccagcaca agggcgtctt cgatggcttc      60
agctacgaga tctggctgga taacaccggc ggtagcggtt ccatgtgtct gggtaaggga     120
gctaccttca aggctgagtg gagcgcagct gtcaaccggg gtaacttcct ggcccgacgc     180
ggtctggatt tcggctccac caagaaggcc accgcttacg agtacatcgg cctggattac     240
gaggcaagct acaggcagac tgccagcgca agcggtaaca gccgcctctg cgtctacggc     300
tggttccaga accggggagt gcagggcgtc cccctggtcg agtactacat catcgaggat     360
tgggtcgact gggtcccgga tgcgcaggga aagatggtca ccatcgatgg cgcccagtac     420
aagatcttcc agatggatca cactggcccg accatcaacg gcggtaacga gaccttcaag     480
cagtacttca gcgtccgcca gcagaagcgc actagcggcc acatcaccgt cagcgatcac     540
ttcaaggcgt gggccaacca gggctggggc atcggcaacc tctacgaggt cacactgaac     600
gcagagggtt ggcagagcag tggtgtcgcc gacgtcacca agctggatgt ctacaccacc     660
aagcagggtt cggcccctcg ttag                                            684
```

<210> SEQ ID NO 5
<211> LENGTH: 227
<212> TYPE: PRT
<213> ORGANISM: Artificial Sequence
<220> FEATURE:
<223> OTHER INFORMATION: DS2(S5C+S34C)

<400> SEQUENCE: 5

```
Gly Gln Arg Leu Cys Val Gly Gly Gly Gln Asn Gln His Lys Gly Val
1               5                   10                  15

Phe Asp Gly Phe Ser Tyr Glu Ile Trp Leu Asp Asn Thr Gly Gly Ser
            20                  25                  30

Gly Cys Met Thr Leu Gly Lys Gly Ala Thr Phe Lys Ala Glu Trp Ser
        35                  40                  45

Ala Ala Val Asn Arg Gly Asn Phe Leu Ala Arg Arg Gly Leu Asp Phe
    50                  55                  60

Gly Ser Thr Lys Lys Ala Thr Ala Tyr Glu Tyr Ile Gly Leu Asp Tyr
65                  70                  75                  80

Glu Ala Ser Tyr Arg Gln Thr Ala Ser Ala Ser Gly Asn Ser Arg Leu
                85                  90                  95

Cys Val Tyr Gly Trp Phe Gln Asn Arg Gly Val Gln Gly Val Pro Leu
            100                 105                 110

Val Glu Tyr Tyr Ile Ile Glu Asp Trp Val Asp Trp Val Pro Asp Ala
        115                 120                 125

Gln Gly Lys Met Val Thr Ile Asp Gly Ala Gln Tyr Lys Ile Phe Gln
    130                 135                 140

Met Asp His Thr Gly Pro Thr Ile Asn Gly Gly Asn Glu Thr Phe Lys
145                 150                 155                 160

Gln Tyr Phe Ser Val Arg Gln Gln Lys Arg Thr Ser Gly His Ile Thr
                165                 170                 175

Val Ser Asp His Phe Lys Ala Trp Ala Asn Gln Gly Trp Gly Ile Gly
            180                 185                 190

Asn Leu Tyr Glu Val Thr Leu Asn Ala Glu Gly Trp Gln Ser Ser Gly
        195                 200                 205
```

-continued

```
Val Ala Asp Val Thr Lys Leu Asp Val Tyr Thr Thr Lys Gln Gly Ser
    210                 215                 220

Ala Pro Arg
225

<210> SEQ ID NO 6
<211> LENGTH: 684
<212> TYPE: DNA
<213> ORGANISM: Artificial Sequence
<220> FEATURE:
<223> OTHER INFORMATION: DS2(S5C+S34C) nt

<400> SEQUENCE: 6
ggccagaggt tgtgtgtcgg tggtggccag aaccagcaca agggcgtctt cgatggcttc      60
agctacgaga tctggctgga taacaccggc ggtagcggtt gtatgaccct gggtaaggga     120
gctaccttca aggctgagtg gagcgcagct gtcaaccggg gtaacttcct ggcccgacgc     180
ggtctggatt tcggctccac caagaaggcc accgcttacg agtacatcgg cctggattac     240
gaggcaagct acaggcagac tgccagcgca agcggtaaca gccgcctctg cgtctacggc     300
tggttccaga accggggagt gcagggcgtc cccctggtcg agtactacat catcgaggat     360
tgggtcgact gggtcccgga tgcgcaggga aagatggtca ccatcgatgg cgcccagtac     420
aagatcttcc agatggatca cactggcccg accatcaacg gcggtaacga gaccttcaag     480
cagtacttca gcgtccgcca gcagaagcgc actagcggcc acatcaccgt cagcgatcac     540
ttcaaggcgt gggccaacca gggctggggc atcggcaacc tctacgaggt cacactgaac     600
gcagagggtt ggcagagcag tggtgtcgcc gacgtcacca agctggatgt ctacaccacc     660
aagcagggtt cggcccctcg ttag                                            684

<210> SEQ ID NO 7
<211> LENGTH: 227
<212> TYPE: PRT
<213> ORGANISM: Artificial Sequence
<220> FEATURE:
<223> OTHER INFORMATION: DS5(F20C+A41C)

<400> SEQUENCE: 7

Gly Gln Arg Leu Ser Val Gly Gly Gln Asn Gln His Lys Gly Val
1               5                   10                  15

Phe Asp Gly Cys Ser Tyr Glu Ile Trp Leu Asp Asn Thr Gly Gly Ser
            20                  25                  30

Gly Ser Met Thr Leu Gly Lys Gly Cys Thr Phe Lys Ala Glu Trp Ser
        35                  40                  45

Ala Ala Val Asn Arg Gly Asn Phe Leu Ala Arg Arg Gly Leu Asp Phe
    50                  55                  60

Gly Ser Thr Lys Lys Ala Thr Ala Tyr Glu Tyr Ile Gly Leu Asp Tyr
65                  70                  75                  80

Glu Ala Ser Tyr Arg Gln Thr Ala Ser Ala Ser Gly Asn Ser Arg Leu
                85                  90                  95

Cys Val Tyr Gly Trp Phe Gln Asn Arg Gly Val Gln Gly Val Pro Leu
            100                 105                 110

Val Glu Tyr Tyr Ile Ile Glu Asp Trp Val Asp Trp Val Pro Asp Ala
            115                 120                 125

Gln Gly Lys Met Val Thr Ile Asp Gly Ala Gln Tyr Lys Ile Phe Gln
    130                 135                 140

Met Asp His Thr Gly Pro Thr Ile Asn Gly Gly Asn Glu Thr Phe Lys
```

-continued

```
145             150             155             160

Gln Tyr Phe Ser Val Arg Gln Gln Lys Arg Thr Ser Gly His Ile Thr
                165             170             175

Val Ser Asp His Phe Lys Ala Trp Ala Asn Gln Gly Trp Gly Ile Gly
            180             185             190

Asn Leu Tyr Glu Val Thr Leu Asn Ala Glu Gly Trp Gln Ser Ser Gly
            195             200             205

Val Ala Asp Val Thr Lys Leu Asp Val Tyr Thr Thr Lys Gln Gly Ser
    210             215             220

Ala Pro Arg
225

<210> SEQ ID NO 8
<211> LENGTH: 684
<212> TYPE: DNA
<213> ORGANISM: Artificial Sequence
<220> FEATURE:
<223> OTHER INFORMATION: DS5(F20C+A41C) nt

<400> SEQUENCE: 8
ggccagaggt tgagcgtcgg tggtggccag aaccagcaca agggcgtctt cgatggctgt      60
agctacgaga tctggctgga taacaccggc ggtagcggtt ccatgaccct gggtaaggga     120
tgtaccttca aggctgagtg gagcgcagct gtcaaccggg gtaacttcct ggcccgacgc     180
ggtctggatt tcggctccac caagaaggcc accgcttacg agtacatcgg cctggattac     240
gaggcaagct acaggcagac tgccagcgca agcggtaaca gccgcctctg cgtctacggc     300
tggttccaga accgggggagt gcagggcgtc cccctggtcg agtactacat catcgaggat     360
tgggtcgact gggtcccgga tgcgcaggga aagatggtca ccatcgatgg cgcccagtac     420
aagatcttcc agatggatca cactggcccg accatcaacg gcggtaacga gaccttcaag     480
cagtacttca gcgtccgcca gcagaagcgc actagcggcc acatcaccgt cagcgatcac     540
ttcaaggcgt gggccaacca gggctggggc atcggcaacc tctacgaggt cacactgaac     600
gcagagggtt ggcagagcag tggtgtcgcc gacgtcacca agctggatgt ctacaccacc     660
aagcagggtt cggcccctcg ttag                                            684

<210> SEQ ID NO 9
<211> LENGTH: 227
<212> TYPE: PRT
<213> ORGANISM: Artificial Sequence
<220> FEATURE:
<223> OTHER INFORMATION: DS1 + SDM4(N52P)

<400> SEQUENCE: 9

Gly Gln Cys Leu Ser Val Gly Gly Gly Gln Asn Gln His Lys Gly Val
1               5               10              15

Phe Asp Gly Phe Ser Tyr Glu Ile Trp Leu Asp Asn Thr Gly Gly Ser
            20              25              30

Gly Ser Met Cys Leu Gly Lys Gly Ala Thr Phe Lys Ala Glu Trp Ser
        35              40              45

Ala Ala Val Pro Arg Gly Asn Phe Leu Ala Arg Arg Gly Leu Asp Phe
    50              55              60

Gly Ser Thr Lys Lys Ala Thr Ala Tyr Glu Tyr Ile Gly Leu Asp Tyr
65              70              75              80

Glu Ala Ser Tyr Arg Gln Thr Ala Ser Ala Ser Gly Asn Ser Arg Leu
            85              90              95
```

```
Cys Val Tyr Gly Trp Phe Gln Asn Arg Gly Val Gln Gly Val Pro Leu
            100                 105                 110

Val Glu Tyr Tyr Ile Ile Glu Asp Trp Val Asp Trp Val Pro Asp Ala
            115                 120                 125

Gln Gly Lys Met Val Thr Ile Asp Gly Ala Gln Tyr Lys Ile Phe Gln
        130                 135                 140

Met Asp His Thr Gly Pro Thr Ile Asn Gly Gly Asn Glu Thr Phe Lys
145                 150                 155                 160

Gln Tyr Phe Ser Val Arg Gln Gln Lys Arg Thr Ser Gly His Ile Thr
                165                 170                 175

Val Ser Asp His Phe Lys Ala Trp Ala Asn Gln Gly Trp Gly Ile Gly
            180                 185                 190

Asn Leu Tyr Glu Val Thr Leu Asn Ala Glu Gly Trp Gln Ser Ser Gly
            195                 200                 205

Val Ala Asp Val Thr Lys Leu Asp Val Tyr Thr Thr Lys Gln Gly Ser
        210                 215                 220

Ala Pro Arg
225

<210> SEQ ID NO 10
<211> LENGTH: 684
<212> TYPE: DNA
<213> ORGANISM: Artificial Sequence
<220> FEATURE:
<223> OTHER INFORMATION: DS1 + SDM4(N52P) nt

<400> SEQUENCE: 10
ggccagtgtt tgagcgtcgg tggtggccag aaccagcaca agggcgtctt cgatggcttc      60
agctacgaga tctggctgga taacaccggc ggtagcggtt ccatgtgtct gggtaaggga     120
gctaccttca aggctgagtg gagcgcagct gtcccccggg gtaacttcct ggcccgacgc     180
ggtctggatt tcggctccac caagaaggcc accgcttacg agtacatcgg cctggattac     240
gaggcaagct acaggcagac tgccagcgca agcggtaaca gccgcctctg cgtctacggc     300
tggttccaga accgggggagt gcagggcgtc cccctggtcg agtactacat catcgaggat     360
tgggtcgact gggtcccgga tgcgcaggga aagatggtca ccatcgatgg cgcccagtac     420
aagatcttcc agatggatca cactggcccg accatcaacg gcggtaacga gaccttcaag     480
cagtacttca gcgtccgcca gcagaagcgc actagcggcc acatcaccgt cagcgatcac     540
ttcaaggcgt gggccaacca gggctggggc atcggcaacc tctacgaggt cacactgaac     600
gcagagggtt ggcagagcag tggtgtcgcc gacgtcacca agctggatgt ctacaccacc     660
aagcagggtt cggcccctcg ttag                                           684

<210> SEQ ID NO 11
<211> LENGTH: 227
<212> TYPE: PRT
<213> ORGANISM: Artificial Sequence
<220> FEATURE:
<223> OTHER INFORMATION: DS1 + SDM7(N28G)

<400> SEQUENCE: 11

Gly Gln Cys Leu Ser Val Gly Gly Gly Gln Asn Gln His Lys Gly Val
1               5                   10                  15

Phe Asp Gly Phe Ser Tyr Glu Ile Trp Leu Asp Gly Thr Gly Gly Ser
                20                  25                  30

Gly Ser Met Cys Leu Gly Lys Gly Ala Thr Phe Lys Ala Glu Trp Ser
        35                  40                  45
```

-continued

Ala Ala Val Asn Arg Gly Asn Phe Leu Ala Arg Arg Gly Leu Asp Phe
     50                  55                  60

Gly Ser Thr Lys Lys Ala Thr Ala Tyr Glu Tyr Ile Gly Leu Asp Tyr
65                  70                  75                  80

Glu Ala Ser Tyr Arg Gln Thr Ala Ser Ala Ser Gly Asn Ser Arg Leu
                 85                  90                  95

Cys Val Tyr Gly Trp Phe Gln Asn Arg Gly Val Gln Gly Val Pro Leu
                 100                 105                 110

Val Glu Tyr Tyr Ile Ile Glu Asp Trp Val Asp Trp Val Pro Asp Ala
                 115                 120                 125

Gln Gly Lys Met Val Thr Ile Asp Gly Ala Gln Tyr Lys Ile Phe Gln
     130                 135                 140

Met Asp His Thr Gly Pro Thr Ile Asn Gly Gly Asn Glu Thr Phe Lys
145                 150                 155                 160

Gln Tyr Phe Ser Val Arg Gln Gln Lys Arg Thr Ser Gly His Ile Thr
                 165                 170                 175

Val Ser Asp His Phe Lys Ala Trp Ala Asn Gln Gly Trp Gly Ile Gly
                 180                 185                 190

Asn Leu Tyr Glu Val Thr Leu Asn Ala Glu Gly Trp Gln Ser Ser Gly
                 195                 200                 205

Val Ala Asp Val Thr Lys Leu Asp Val Tyr Thr Thr Lys Gln Gly Ser
     210                 215                 220

Ala Pro Arg
225

<210> SEQ ID NO 12
<211> LENGTH: 684
<212> TYPE: DNA
<213> ORGANISM: Artificial Sequence
<220> FEATURE:
<223> OTHER INFORMATION: DS1 + SDM7(N28G) nt

<400> SEQUENCE: 12
ggccagtgtt tgagcgtcgg tggtggccag aaccagcaca agggcgtctt cgatggcttc      60
agctacgaga tctggctgga tggcaccggc ggtagcggtt ccatgtgtct gggtaaggga     120
gctaccttca aggctgagtg gagcgcagct gtcaaccggg gtaacttcct ggcccgacgc     180
ggtctggatt tcggctccac caagaaggcc accgcttacg agtacatcgg cctggattac     240
gaggcaagct acaggcagac tgccagcgca agcggtaaca gccgcctctg cgtctacggc     300
tggttccaga accggggagt gcaggggcgtc cccctggtcg agtactacat catcgaggat     360
tgggtcgact gggtcccgga tgcgcaggga agatggtca ccatcgatgg cgcccagtac      420
aagatcttcc agatggatca cactggcccg accatcaacg gcggtaacga gaccttcaag     480
cagtacttca gcgtccgcca gcagaagcgc actagcggcc acatcaccgt cagcgatcac     540
ttcaaggcgt gggccaacca gggctggggc atcggcaacc tctacgaggt cacactgaac     600
gcagagggtt ggcagagcag tggtgtcgcc gacgtcacca agctggatgt ctacaccacc     660
aagcagggtt cggcccctcg ttag                                           684

<210> SEQ ID NO 13
<211> LENGTH: 227
<212> TYPE: PRT
<213> ORGANISM: Artificial Sequence
<220> FEATURE:
<223> OTHER INFORMATION: DS1 + SDM4+SDM7(N52P+N28G)

```
<400> SEQUENCE: 13

Gly Gln Cys Leu Ser Val Gly Gly Gly Gln Asn Gln His Lys Gly Val
1               5                   10                  15

Phe Asp Gly Phe Ser Tyr Glu Ile Trp Leu Asp Gly Thr Gly Gly Ser
                20                  25                  30

Gly Ser Met Cys Leu Gly Lys Gly Ala Thr Phe Lys Ala Glu Trp Ser
                35                  40                  45

Ala Ala Val Pro Arg Gly Asn Phe Leu Ala Arg Arg Gly Leu Asp Phe
        50                  55                  60

Gly Ser Thr Lys Lys Ala Thr Ala Tyr Glu Tyr Ile Gly Leu Asp Tyr
65                  70                  75                  80

Glu Ala Ser Tyr Arg Gln Thr Ala Ser Ala Ser Gly Asn Ser Arg Leu
                85                  90                  95

Cys Val Tyr Gly Trp Phe Gln Asn Arg Gly Val Gln Gly Val Pro Leu
                100                 105                 110

Val Glu Tyr Tyr Ile Ile Glu Asp Trp Val Asp Trp Val Pro Asp Ala
                115                 120                 125

Gln Gly Lys Met Val Thr Ile Asp Gly Ala Gln Tyr Lys Ile Phe Gln
        130                 135                 140

Met Asp His Thr Gly Pro Thr Ile Asn Gly Gly Asn Glu Thr Phe Lys
145                 150                 155                 160

Gln Tyr Phe Ser Val Arg Gln Gln Lys Arg Thr Ser Gly His Ile Thr
                165                 170                 175

Val Ser Asp His Phe Lys Ala Trp Ala Asn Gln Gly Trp Gly Ile Gly
                180                 185                 190

Asn Leu Tyr Glu Val Thr Leu Asn Ala Glu Gly Trp Gln Ser Ser Gly
                195                 200                 205

Val Ala Asp Val Thr Lys Leu Asp Val Tyr Thr Thr Lys Gln Gly Ser
        210                 215                 220

Ala Pro Arg
225

<210> SEQ ID NO 14
<211> LENGTH: 684
<212> TYPE: DNA
<213> ORGANISM: Artificial Sequence
<220> FEATURE:
<223> OTHER INFORMATION: DS1 + SDM4+SDM7(N52P+N28G)

<400> SEQUENCE: 14
ggccagtgtt tgagcgtcgg tggtggccag aaccagcaca agggcgtctt cgatggcttc      60
agctacgaga tctggctgga tggcaccggc ggtagcggtt ccatgtgtct gggtaaggga     120
gctaccttca aggctgagtg gagcgcagct gtcccccggg gtaacttcct ggcccgacgc     180
ggtctggatt tcggctccac caagaaggcc accgcttacg agtacatcgg cctggattac     240
gaggcaagct acaggcagac tgccagcgca agcggtaaca gccgcctctg cgtctacggc     300
tggttccaga accgggagt gcagggcgtc cccctggtcg agtactacat catcgaggat     360
tgggtcgact gggtcccgga tgcgcaggga aagatggtca ccatcgatgg cgcccagtac     420
aagatcttcc agatggatca cactggcccg accatcaacg gcggtaacga gaccttcaag     480
cagtacttca gcgtccgcca gcagaagcgc actagcggcc acatcaccgt cagcgatcac     540
ttcaaggcgt gggccaacca gggctgggc atcggcaacc tctacgaggt cacactgaac     600
gcagagggtt ggcagagcag tggtgtcgcc gacgtcacca agctggatgt ctacaccacc     660
```

-continued

```
aagcagggtt cggcccctcg ttag                                              684
```

```
<210> SEQ ID NO 15
<211> LENGTH: 227
<212> TYPE: PRT
<213> ORGANISM: Artificial Sequence
<220> FEATURE:
<223> OTHER INFORMATION: DS2 + SDM4(N52P)

<400> SEQUENCE: 15

Gly Gln Arg Leu Cys Val Gly Gly Gln Asn Gln His Lys Gly Val
1               5                   10                  15

Phe Asp Gly Phe Ser Tyr Glu Ile Trp Leu Asp Asn Thr Gly Gly Ser
            20                  25                  30

Gly Cys Met Thr Leu Gly Lys Gly Ala Thr Phe Lys Ala Glu Trp Ser
        35                  40                  45

Ala Ala Val Pro Arg Gly Asn Phe Leu Ala Arg Arg Gly Leu Asp Phe
    50                  55                  60

Gly Ser Thr Lys Lys Ala Thr Ala Tyr Glu Tyr Ile Gly Leu Asp Tyr
65                  70                  75                  80

Glu Ala Ser Tyr Arg Gln Thr Ala Ser Ala Ser Gly Asn Ser Arg Leu
                85                  90                  95

Cys Val Tyr Gly Trp Phe Gln Asn Arg Gly Val Gln Gly Val Pro Leu
            100                 105                 110

Val Glu Tyr Tyr Ile Ile Glu Asp Trp Val Asp Trp Val Pro Asp Ala
            115                 120                 125

Gln Gly Lys Met Val Thr Ile Asp Gly Ala Gln Tyr Lys Ile Phe Gln
        130                 135                 140

Met Asp His Thr Gly Pro Thr Ile Asn Gly Gly Asn Glu Thr Phe Lys
145                 150                 155                 160

Gln Tyr Phe Ser Val Arg Gln Gln Lys Arg Thr Ser Gly His Ile Thr
                165                 170                 175

Val Ser Asp His Phe Lys Ala Trp Ala Asn Gln Gly Trp Gly Ile Gly
            180                 185                 190

Asn Leu Tyr Glu Val Thr Leu Asn Ala Glu Gly Trp Gln Ser Ser Gly
        195                 200                 205

Val Ala Asp Val Thr Lys Leu Asp Val Tyr Thr Thr Lys Gln Gly Ser
    210                 215                 220

Ala Pro Arg
225
```

```
<210> SEQ ID NO 16
<211> LENGTH: 684
<212> TYPE: DNA
<213> ORGANISM: Artificial Sequence
<220> FEATURE:
<223> OTHER INFORMATION: DS2 + SDM4(N52P)

<400> SEQUENCE: 16
ggccagaggt tgtgtgtcgg tggtggccag aaccagcaca agggcgtctt cgatggcttc      60
agctacgaga tctggctgga taacaccggc ggtagcggtt gtatgaccct gggtaaggga     120
gctaccttca aggctgagtg gagcgcagct gtcccccggg gtaacttcct ggcccgacgc     180
ggtctggatt tcggctccac caagaaggcc accgcttacg agtacatcgg cctggattac     240
gaggcaagct acaggcagac tgccagcgca agcggtaaca gccgcctctg cgtctacggc     300
tggttccaga accgggggagt gcagggcgtc cccctggtcg agtactacat catcgaggat     360
```

-continued

```
tgggtcgact gggtcccgga tgcgcaggga aagatggtca ccatcgatgg cgcccagtac      420
aagatcttcc agatggatca cactggcccg accatcaacg gcggtaacga gaccttcaag      480
cagtacttca gcgtccgcca gcagaagcgc actagcggcc acatcaccgt cagcgatcac      540
ttcaaggcgt gggccaacca gggctggggc atcggcaacc tctacgaggt cacactgaac      600
gcagagggtt ggcagagcag tggtgtcgcc gacgtcacca agctggatgt ctacaccacc      660
aagcagggtt cggcccctcg ttag                                            684
```

<210> SEQ ID NO 17
<211> LENGTH: 227
<212> TYPE: PRT
<213> ORGANISM: Artificial Sequence
<220> FEATURE:
<223> OTHER INFORMATION: DS2 + SDM7(N28G)

<400> SEQUENCE: 17

```
Gly Gln Arg Leu Cys Val Gly Gly Gln Asn Gln His Lys Gly Val
1               5                   10                  15

Phe Asp Gly Phe Ser Tyr Glu Ile Trp Leu Asp Gly Thr Gly Gly Ser
            20                  25                  30

Gly Cys Met Thr Leu Gly Lys Gly Ala Thr Phe Lys Ala Glu Trp Ser
        35                  40                  45

Ala Ala Val Asn Arg Gly Asn Phe Leu Ala Arg Arg Gly Leu Asp Phe
    50                  55                  60

Gly Ser Thr Lys Lys Ala Thr Ala Tyr Glu Tyr Ile Gly Leu Asp Tyr
65                  70                  75                  80

Glu Ala Ser Tyr Arg Gln Thr Ala Ser Ala Ser Gly Asn Ser Arg Leu
                85                  90                  95

Cys Val Tyr Gly Trp Phe Gln Asn Arg Gly Val Gln Gly Val Pro Leu
            100                 105                 110

Val Glu Tyr Tyr Ile Ile Glu Asp Trp Val Asp Trp Val Pro Asp Ala
        115                 120                 125

Gln Gly Lys Met Val Thr Ile Asp Gly Ala Gln Tyr Lys Ile Phe Gln
    130                 135                 140

Met Asp His Thr Gly Pro Thr Ile Asn Gly Gly Asn Glu Thr Phe Lys
145                 150                 155                 160

Gln Tyr Phe Ser Val Arg Gln Gln Lys Arg Thr Ser Gly His Ile Thr
                165                 170                 175

Val Ser Asp His Phe Lys Ala Trp Ala Asn Gln Gly Trp Gly Ile Gly
            180                 185                 190

Asn Leu Tyr Glu Val Thr Leu Asn Ala Glu Gly Trp Gln Ser Ser Gly
        195                 200                 205

Val Ala Asp Val Thr Lys Leu Asp Val Tyr Thr Thr Lys Gln Gly Ser
    210                 215                 220

Ala Pro Arg
225
```

<210> SEQ ID NO 18
<211> LENGTH: 684
<212> TYPE: DNA
<213> ORGANISM: Artificial Sequence
<220> FEATURE:
<223> OTHER INFORMATION: DS2 + SDM7(N28G) nt

<400> SEQUENCE: 18

```
ggccagaggt tgtgtgtcgg tggtggccag aaccagcaca agggcgtctt cgatggcttc       60
```

-continued

```
agctacgaga tctggctgga tggcaccggc ggtagcggtt gtatgaccct gggtaaggga    120
gctaccttca aggctgagtg gagcgcagct gtcaaccggg gtaacttcct ggcccgacgc    180
ggtctggatt tcggctccac caagaaggcc accgcttacg agtacatcgg cctggattac    240
gaggcaagct acaggcagac tgccagcgca agcggtaaca gccgcctctg cgtctacggc    300
tggttccaga accggggagt gcagggcgtc cccctggtcg agtactacat catcgaggat    360
tgggtcgact gggtcccgga tgcgcaggga aagatggtca ccatcgatgg cgcccagtac    420
aagatcttcc agatggatca cactggcccg accatcaacg gcggtaacga gaccttcaag    480
cagtacttca gcgtccgcca gcagaagcgc actagcggcc acatcaccgt cagcgatcac    540
ttcaaggcgt gggccaacca gggctggggc atcggcaacc tctacgaggt cacactgaac    600
gcagagggtt ggcagagcag tggtgtcgcc gacgtcacca agctggatgt ctacaccacc    660
aagcagggtt cggcccctcg ttag                                           684
```

```
<210> SEQ ID NO 19
<211> LENGTH: 227
<212> TYPE: PRT
<213> ORGANISM: Artificial Sequence
<220> FEATURE:
<223> OTHER INFORMATION: DS2 + SDM4+SDM7(N52P+N28G)

<400> SEQUENCE: 19

Gly Gln Arg Leu Cys Val Gly Gly Gly Gln Asn Gln His Lys Gly Val
1               5                   10                  15

Phe Asp Gly Phe Ser Tyr Glu Ile Trp Leu Asp Gly Thr Gly Gly Ser
            20                  25                  30

Gly Cys Met Thr Leu Gly Lys Gly Ala Thr Phe Lys Ala Glu Trp Ser
        35                  40                  45

Ala Ala Val Pro Arg Gly Asn Phe Leu Ala Arg Arg Gly Leu Asp Phe
    50                  55                  60

Gly Ser Thr Lys Lys Ala Thr Ala Tyr Glu Tyr Ile Gly Leu Asp Tyr
65                  70                  75                  80

Glu Ala Ser Tyr Arg Gln Thr Ala Ser Ala Ser Gly Asn Ser Arg Leu
                85                  90                  95

Cys Val Tyr Gly Trp Phe Gln Asn Arg Gly Val Gln Gly Val Pro Leu
            100                 105                 110

Val Glu Tyr Tyr Ile Ile Glu Asp Trp Val Asp Trp Val Pro Asp Ala
            115                 120                 125

Gln Gly Lys Met Val Thr Ile Asp Gly Ala Gln Tyr Lys Ile Phe Gln
    130                 135                 140

Met Asp His Thr Gly Pro Thr Ile Asn Gly Gly Asn Glu Thr Phe Lys
145                 150                 155                 160

Gln Tyr Phe Ser Val Arg Gln Gln Lys Arg Thr Ser Gly His Ile Thr
                165                 170                 175

Val Ser Asp His Phe Lys Ala Trp Ala Asn Gln Gly Trp Gly Ile Gly
            180                 185                 190

Asn Leu Tyr Glu Val Thr Leu Asn Ala Glu Gly Trp Gln Ser Ser Gly
            195                 200                 205

Val Ala Asp Val Thr Lys Leu Asp Val Tyr Thr Thr Lys Gln Gly Ser
    210                 215                 220

Ala Pro Arg
225

<210> SEQ ID NO 20
```

```
<211> LENGTH: 684
<212> TYPE: DNA
<213> ORGANISM: Artificial Sequence
<220> FEATURE:
<223> OTHER INFORMATION: DS2 + SDM4+SDM7(N52P+N28G) nt

<400> SEQUENCE: 20
ggccagaggt tgtgtgtcgg tggtggccag aaccagcaca agggcgtctt cgatggcttc      60
agctacgaga tctggctgga tggcaccggc ggtagcggtt gtatgaccct gggtaaggga     120
gctaccttca aggctgagtg gagcgcagct gtcccccggg gtaacttcct ggcccgacgc     180
ggtctggatt tcggctccac caagaaggcc accgcttacg agtacatcgg cctggattac     240
gaggcaagct acaggcagac tgccagcgca agcggtaaca gccgcctctg cgtctacggc     300
tggttccaga accggggagt gcagggcgtc cccctggtcg agtactacat catcgaggat     360
tgggtcgact gggtcccgga tgcgcaggga agatggtca ccatcgatgg cgcccagtac      420
aagatcttcc agatggatca cactggcccg accatcaacg gcggtaacga gaccttcaag     480
cagtacttca gcgtccgcca gcagaagcgc actagcggcc acatcaccgt cagcgatcac     540
ttcaaggcgt gggccaacca gggctggggc atcggcaacc tctacgaggt cacactgaac     600
gcagagggtt ggcagagcag tggtgtcgcc gacgtcacca agctggatgt ctacaccacc     660
aagcagggtt cggcccctcg ttag     684

<210> SEQ ID NO 21
<211> LENGTH: 227
<212> TYPE: PRT
<213> ORGANISM: Artificial Sequence
<220> FEATURE:
<223> OTHER INFORMATION: DS5 + SDM4(N52P)

<400> SEQUENCE: 21

Gly Gln Arg Leu Ser Val Gly Gly Gly Gln Asn Gln His Lys Gly Val
1                5                   10                  15

Phe Asp Gly Cys Ser Tyr Glu Ile Trp Leu Asp Asn Thr Gly Gly Ser
                20                  25                  30

Gly Ser Met Thr Leu Gly Lys Gly Cys Thr Phe Lys Ala Glu Trp Ser
            35                  40                  45

Ala Ala Val Pro Arg Gly Asn Phe Leu Ala Arg Arg Gly Leu Asp Phe
        50                  55                  60

Gly Ser Thr Lys Lys Ala Thr Ala Tyr Glu Tyr Ile Gly Leu Asp Tyr
65                  70                  75                  80

Glu Ala Ser Tyr Arg Gln Thr Ala Ser Ala Ser Gly Asn Ser Arg Leu
                85                  90                  95

Cys Val Tyr Gly Trp Phe Gln Asn Arg Gly Val Gln Gly Val Pro Leu
            100                 105                 110

Val Glu Tyr Tyr Ile Ile Glu Asp Trp Val Asp Trp Val Pro Asp Ala
        115                 120                 125

Gln Gly Lys Met Val Thr Ile Asp Gly Ala Gln Tyr Lys Ile Phe Gln
        130                 135                 140

Met Asp His Thr Gly Pro Thr Ile Asn Gly Gly Asn Glu Thr Phe Lys
145                 150                 155                 160

Gln Tyr Phe Ser Val Arg Gln Gln Lys Arg Thr Ser Gly His Ile Thr
                165                 170                 175

Val Ser Asp His Phe Lys Ala Trp Ala Asn Gln Gly Trp Gly Ile Gly
            180                 185                 190

Asn Leu Tyr Glu Val Thr Leu Asn Ala Glu Gly Trp Gln Ser Ser Gly
```

-continued

```
                   195                 200                 205
Val Ala Asp Val Thr Lys Leu Asp Val Tyr Thr Thr Lys Gln Gly Ser
    210                 215                 220

Ala Pro Arg
225

<210> SEQ ID NO 22
<211> LENGTH: 684
<212> TYPE: DNA
<213> ORGANISM: Artificial Sequence
<220> FEATURE:
<223> OTHER INFORMATION: DS5 + SDM4(N52P) nt

<400> SEQUENCE: 22
ggccagaggt tgagcgtcgg tggtggccag aaccagcaca agggcgtctt cgatggctgt     60
agctacgaga tctggctgga taacaccggc ggtagcggtt ccatgaccct gggtaaggga    120
tgtaccttca aggctgagtg gagcgcagct gtccccgggg gtaacttcct ggcccgacgc    180
ggtctggatt tcggctccac caagaaggcc accgcttacg agtacatcgg cctggattac    240
gaggcaagct acaggcagac tgccagcgca agcggtaaca gccgcctctg cgtctacggc    300
tggttccaga accggggagt gcagggcgtc cccctggtcg agtactacat catcgaggat    360
tgggtcgact gggtcccgga tgcgcaggga aagatggtca ccatcgatgg cgcccagtac    420
aagatcttcc agatggatca cactggcccg accatcaacg gcggtaacga gaccttcaag    480
cagtacttca gcgtccgcca gcagaagcgc actagcggcc acatcaccgt cagcgatcac    540
ttcaaggcgt gggccaacca gggctggggc atcggcaacc tctacgaggt cacactgaac    600
gcagagggtt ggcagagcag tggtgtcgcc gacgtcacca agctggatgt ctacaccacc    660
aagcagggtt cggcccctcg ttag                                           684

<210> SEQ ID NO 23
<211> LENGTH: 227
<212> TYPE: PRT
<213> ORGANISM: Artificial Sequence
<220> FEATURE:
<223> OTHER INFORMATION: DS5 + SDM7(N28G)

<400> SEQUENCE: 23

Gly Gln Arg Leu Ser Val Gly Gly Gln Asn Gln His Lys Gly Val
1               5                   10                  15

Phe Asp Gly Cys Ser Tyr Glu Ile Trp Leu Asp Gly Thr Gly Gly Ser
            20                  25                  30

Gly Ser Met Thr Leu Gly Lys Gly Cys Thr Phe Lys Ala Glu Trp Ser
        35                  40                  45

Ala Ala Val Asn Arg Gly Asn Phe Leu Ala Arg Arg Gly Leu Asp Phe
    50                  55                  60

Gly Ser Thr Lys Lys Ala Thr Ala Tyr Glu Tyr Ile Gly Leu Asp Tyr
65                  70                  75                  80

Glu Ala Ser Tyr Arg Gln Thr Ala Ser Ala Ser Gly Asn Ser Arg Leu
                85                  90                  95

Cys Val Tyr Gly Trp Phe Gln Asn Arg Gly Val Gln Gly Val Pro Leu
            100                 105                 110

Val Glu Tyr Tyr Ile Ile Glu Asp Trp Val Asp Trp Val Pro Asp Ala
        115                 120                 125

Gln Gly Lys Met Val Thr Ile Asp Gly Ala Gln Tyr Lys Ile Phe Gln
    130                 135                 140
```

-continued

```
Met Asp His Thr Gly Pro Thr Ile Asn Gly Gly Asn Glu Thr Phe Lys
145             150                 155                 160

Gln Tyr Phe Ser Val Arg Gln Gln Lys Arg Thr Ser Gly His Ile Thr
            165                 170                 175

Val Ser Asp His Phe Lys Ala Trp Ala Asn Gln Gly Trp Gly Ile Gly
                180             185                 190

Asn Leu Tyr Glu Val Thr Leu Asn Ala Glu Gly Trp Gln Ser Ser Gly
            195                 200             205

Val Ala Asp Val Thr Lys Leu Asp Val Tyr Thr Thr Lys Gln Gly Ser
        210                 215                 220

Ala Pro Arg
225

<210> SEQ ID NO 24
<211> LENGTH: 684
<212> TYPE: DNA
<213> ORGANISM: Artificial Sequence
<220> FEATURE:
<223> OTHER INFORMATION: DS5 + SDM7(N28G) nt

<400> SEQUENCE: 24
ggccagaggt tgagcgtcgg tggtggccag aaccagcaca agggcgtctt cgatggctgt      60
agctacgaga tctggctgga tggcaccggc ggtagcggtt ccatgaccct gggtaaggga     120
tgtaccttca aggctgagtg gagcgcagct gtcaaccggg gtaacttcct ggcccgacgc     180
ggtctggatt tcggctccac caagaaggcc accgcttacg agtacatcgg cctggattac     240
gaggcaagct acaggcagac tgccagcgca agcggtaaca gccgcctctg cgtctacggc     300
tggttccaga accggggagt gcagggcgtc cccctggtcg agtactacat catcgaggat     360
tgggtcgact gggtcccgga tgcgcaggga aagatggtca ccatcgatgg cgcccagtac     420
aagatcttcc agatggatca cactggcccg accatcaacg gcggtaacga gaccttcaag     480
cagtacttca gcgtccgcca gcagaagcgc actagcggcc acatcaccgt cagcgatcac     540
ttcaaggcgt gggccaacca gggctggggc atcggcaacc tctacgaggt cacactgaac     600
gcagagggtt ggcagagcag tggtgtcgcc gacgtcacca agctggatgt ctacaccacc     660
aagcagggtt cggcccctcg ttag                                           684

<210> SEQ ID NO 25
<211> LENGTH: 227
<212> TYPE: PRT
<213> ORGANISM: Artificial Sequence
<220> FEATURE:
<223> OTHER INFORMATION: DS5 + SDM4+SDM7(N52P+N28G)

<400> SEQUENCE: 25

Gly Gln Arg Leu Ser Val Gly Gly Gly Gln Asn Gln His Lys Gly Val
1               5                   10                  15

Phe Asp Gly Cys Ser Tyr Glu Ile Trp Leu Asp Gly Thr Gly Gly Ser
                20                  25                  30

Gly Ser Met Thr Leu Gly Lys Gly Cys Thr Phe Lys Ala Glu Trp Ser
            35                  40                  45

Ala Ala Val Pro Arg Gly Asn Phe Leu Ala Arg Arg Gly Leu Asp Phe
        50                  55                  60

Gly Ser Thr Lys Lys Ala Thr Ala Tyr Glu Tyr Ile Gly Leu Asp Tyr
65                  70                  75                  80

Glu Ala Ser Tyr Arg Gln Thr Ala Ser Ala Ser Gly Asn Ser Arg Leu
                85                  90                  95
```

-continued

```
Cys Val Tyr Gly Trp Phe Gln Asn Arg Gly Val Gln Gly Val Pro Leu
            100                 105                 110

Val Glu Tyr Tyr Ile Ile Glu Asp Trp Val Asp Trp Val Pro Asp Ala
            115                 120                 125

Gln Gly Lys Met Val Thr Ile Asp Gly Ala Gln Tyr Lys Ile Phe Gln
    130                 135                 140

Met Asp His Thr Gly Pro Thr Ile Asn Gly Gly Asn Glu Thr Phe Lys
145                 150                 155                 160

Gln Tyr Phe Ser Val Arg Gln Gln Lys Arg Thr Ser Gly His Ile Thr
                165                 170                 175

Val Ser Asp His Phe Lys Ala Trp Ala Asn Gln Gly Trp Gly Ile Gly
            180                 185                 190

Asn Leu Tyr Glu Val Thr Leu Asn Ala Glu Gly Trp Gln Ser Ser Gly
        195                 200                 205

Val Ala Asp Val Thr Lys Leu Asp Val Tyr Thr Thr Lys Gln Gly Ser
    210                 215                 220

Ala Pro Arg
225
```

```
<210> SEQ ID NO 26
<211> LENGTH: 684
<212> TYPE: DNA
<213> ORGANISM: Artificial Sequence
<220> FEATURE:
<223> OTHER INFORMATION: DS5 + SDM4+SDM7(N52P+N28G) nt

<400> SEQUENCE: 26
ggccagaggt tgagcgtcgg tggtggccag aaccagcaca agggcgtctt cgatggctgt       60
agctacgaga tctggctgga tggcaccggc ggtagcggtt ccatgaccct gggtaaggga      120
tgtaccttca aggctgagtg gagcgcagct gtccccgggg gtaacttcct ggcccgacgc      180
ggtctggatt tcggctccac caagaaggcc accgcttacg agtacatcgg cctggattac      240
gaggcaagct acaggcagac tgccagcgca agcggtaaca gccgcctctg cgtctacggc      300
tggttccaga accggggagt gcagggcgtc cccctggtcg agtactacat catcgaggat      360
tgggtcgact gggtcccgga tgcgcaggga aagatggtca ccatcgatgg cgcccagtac      420
aagatcttcc agatggatca cactggcccg accatcaacg gcggtaacga gaccttcaag      480
cagtacttca gcgtccgcca gcagaagcgc actagcggcc acatcaccgt cagcgatcac      540
ttcaaggcgt gggccaacca gggctggggc atcggcaacc tctacgaggt cacactgaac      600
gcagagggtt ggcagagcag tggtgtcgcc gacgtcacca agctggatgt ctacaccacc      660
aagcagggtt cggcccctcg ttag                                            684
```

```
<210> SEQ ID NO 27
<211> LENGTH: 27
<212> TYPE: DNA
<213> ORGANISM: Artificial Sequence
<220> FEATURE:
<223> OTHER INFORMATION: primer

<400> SEQUENCE: 27
tggttccaga acgatggagt gcagggc                                          27
```

```
<210> SEQ ID NO 28
<211> LENGTH: 19
<212> TYPE: DNA
<213> ORGANISM: Artificial Sequence
```

-continued

```
<220> FEATURE:
<223> OTHER INFORMATION: primer

<400> SEQUENCE: 28
gttctggaac cagccgtag                                                19

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29
tggttccaga acaacggagt gcagggc                                        27

<210> SEQ ID NO 30
<211> LENGTH: 19
<212> TYPE: DNA
<213> ORGANISM: Artificial Sequence
<220> FEATURE:
<223> OTHER INFORMATION: primer

<400> SEQUENCE: 30
gttctggaac cagccgtag                                                19

<210> SEQ ID NO 31
<211> LENGTH: 26
<212> TYPE: DNA
<213> ORGANISM: Artificial Sequence
<220> FEATURE:
<223> OTHER INFORMATION: primer

<400> SEQUENCE: 31
agactgccag cgcaaacggt aacagc                                        26

<210> SEQ ID NO 32
<211> LENGTH: 17
<212> TYPE: DNA
<213> ORGANISM: Artificial Sequence
<220> FEATURE:
<223> OTHER INFORMATION: primer

<400> SEQUENCE: 32
tgcgctggca gtctgcc                                                  17

<210> SEQ ID NO 33
<211> LENGTH: 24
<212> TYPE: DNA
<213> ORGANISM: Artificial Sequence
<220> FEATURE:
<223> OTHER INFORMATION: primer

<400> SEQUENCE: 33
agcgcagctg tcccccgggg taac                                          24

<210> SEQ ID NO 34
<211> LENGTH: 18
<212> TYPE: DNA
<213> ORGANISM: Artificial Sequence
<220> FEATURE:
<223> OTHER INFORMATION: primer

<400> SEQUENCE: 34
gacagctgcg ctccactc                                                 18
```

-continued

```
<210> SEQ ID NO 35
<211> LENGTH: 27
<212> TYPE: DNA
<213> ORGANISM: Artificial Sequence
<220> FEATURE:
<223> OTHER INFORMATION: primer

<400> SEQUENCE: 35
ctggatttcg gcggtaccaa gaaggcc                                        27

<210> SEQ ID NO 36
<211> LENGTH: 18
<212> TYPE: DNA
<213> ORGANISM: Artificial Sequence
<220> FEATURE:
<223> OTHER INFORMATION: primer

<400> SEQUENCE: 36
gccgaaatcc agaccgcg                                                  18

<210> SEQ ID NO 37
<211> LENGTH: 27
<212> TYPE: DNA
<213> ORGANISM: Artificial Sequence
<220> FEATURE:
<223> OTHER INFORMATION: primer

<400> SEQUENCE: 37
ctggatttcg gcaacaccaa gaaggcc                                        27

<210> SEQ ID NO 38
<211> LENGTH: 18
<212> TYPE: DNA
<213> ORGANISM: Artificial Sequence
<220> FEATURE:
<223> OTHER INFORMATION: primer

<400> SEQUENCE: 38
gccgaaatcc agaccgcg                                                  18

<210> SEQ ID NO 39
<211> LENGTH: 23
<212> TYPE: DNA
<213> ORGANISM: Artificial Sequence
<220> FEATURE:
<223> OTHER INFORMATION: primer

<400> SEQUENCE: 39
atctggctgg atggcaccgg cgg                                            23

<210> SEQ ID NO 40
<211> LENGTH: 16
<212> TYPE: DNA
<213> ORGANISM: Artificial Sequence
<220> FEATURE:
<223> OTHER INFORMATION: primer

<400> SEQUENCE: 40
atccagccag atctcg                                                    16

<210> SEQ ID NO 41
<211> LENGTH: 18
<212> TYPE: DNA
<213> ORGANISM: Artificial Sequence
<220> FEATURE:
<223> OTHER INFORMATION: primer
```

```
<400> SEQUENCE: 41
accgtcatcg atcacttc                                                18

<210> SEQ ID NO 42
<211> LENGTH: 18
<212> TYPE: DNA
<213> ORGANISM: Artificial Sequence
<220> FEATURE:
<223> OTHER INFORMATION: primer

<400> SEQUENCE: 42
gtgatcgatg acggtgat                                                18

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
aagcagtggt tcagcgtccg c                                            21

<210> SEQ ID NO 44
<211> LENGTH: 24
<212> TYPE: DNA
<213> ORGANISM: Artificial Sequence
<220> FEATURE:
<223> OTHER INFORMATION: primer

<400> SEQUENCE: 44
gctgaaccac tgcttgaagg tctc                                         24

<210> SEQ ID NO 45
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (15)..(16)
<223> OTHER INFORMATION: n is a, c, g, or t

<400> SEQUENCE: 45
agactgccag cgcannkggt aacagc                                       26

<210> SEQ ID NO 46
<211> LENGTH: 17
<212> TYPE: DNA
<213> ORGANISM: Artificial Sequence
<220> FEATURE:
<223> OTHER INFORMATION: primer

<400> SEQUENCE: 46
tgcgctggca gtctgcc                                                 17

<210> SEQ ID NO 47
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (13)..(14)
```

<223> OTHER INFORMATION: n is a, c, g, or t

<400> SEQUENCE: 47
agcgcagctg tcnnkcgggg taac                                              24

<210> SEQ ID NO 48
<211> LENGTH: 18
<212> TYPE: DNA
<213> ORGANISM: Artificial Sequence
<220> FEATURE:
<223> OTHER INFORMATION: primer

<400> SEQUENCE: 48
gacagctgcg ctccactc                                                     18

<210> SEQ ID NO 49
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (13)..(14)
<223> OTHER INFORMATION: n is a, c, g, or t

<400> SEQUENCE: 49
atctggctgg atnnkaccgg cggtag                                            26

<210> SEQ ID NO 50
<211> LENGTH: 16
<212> TYPE: DNA
<213> ORGANISM: Artificial Sequence
<220> FEATURE:
<223> OTHER INFORMATION: primer

<400> SEQUENCE: 50
atccagccag atctcg                                                       16

<210> SEQ ID NO 51
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (13)..(14)
<223> OTHER INFORMATION: n is a, c, g, or t

<400> SEQUENCE: 51
ttgagcgtcg gtnnkggcca gaacc                                             25

<210> SEQ ID NO 52
<211> LENGTH: 18
<212> TYPE: DNA
<213> ORGANISM: Artificial Sequence
<220> FEATURE:
<223> OTHER INFORMATION: primer

<400> SEQUENCE: 52
accgacgctc aacctctg                                                     18

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
ggccagtgtt tgagcgtcgg                                                     20

<210> SEQ ID NO 54
<211> LENGTH: 22
<212> TYPE: DNA
<213> ORGANISM: Artificial Sequence
<220> FEATURE:
<223> OTHER INFORMATION: primer

<400> SEQUENCE: 54
gctcaaacac tggcccatat gg                                                  22

<210> SEQ ID NO 55
<211> LENGTH: 24
<212> TYPE: DNA
<213> ORGANISM: Artificial Sequence
<220> FEATURE:
<223> OTHER INFORMATION: primer

<400> SEQUENCE: 55
aagggatgta ccttcaaggc tgag                                                24

<210> SEQ ID NO 56
<211> LENGTH: 24
<212> TYPE: DNA
<213> ORGANISM: Artificial Sequence
<220> FEATURE:
<223> OTHER INFORMATION: primer

<400> SEQUENCE: 56
acccagacac atggaaccgc tacc                                                24

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
aggttgtgtg tcggtggtgg                                                     20

<210> SEQ ID NO 58
<211> LENGTH: 21
<212> TYPE: DNA
<213> ORGANISM: Artificial Sequence
<220> FEATURE:
<223> OTHER INFORMATION: primer

<400> SEQUENCE: 58
accgacacac aacctctggc c                                                   21

<210> SEQ ID NO 59
<211> LENGTH: 24
<212> TYPE: DNA
<213> ORGANISM: Artificial Sequence
<220> FEATURE:
<223> OTHER INFORMATION: primer

<400> SEQUENCE: 59
agcggttgta tgaccctggg taag                                                24

-continued

```
<210> SEQ ID NO 60
<211> LENGTH: 21
<212> TYPE: DNA
<213> ORGANISM: Artificial Sequence
<220> FEATURE:
<223> OTHER INFORMATION: primer

<400> SEQUENCE: 60
ggtcatacaa ccgctaccgc c                                              21

<210> SEQ ID NO 61
<211> LENGTH: 26
<212> TYPE: DNA
<213> ORGANISM: Artificial Sequence
<220> FEATURE:
<223> OTHER INFORMATION: primer

<400> SEQUENCE: 61
ccggattgtc agggaaagat ggtcac                                         26

<210> SEQ ID NO 62
<211> LENGTH: 22
<212> TYPE: DNA
<213> ORGANISM: Artificial Sequence
<220> FEATURE:
<223> OTHER INFORMATION: primer

<400> SEQUENCE: 62
tccctgacaa tccgggaccc ag                                             22

<210> SEQ ID NO 63
<211> LENGTH: 26
<212> TYPE: DNA
<213> ORGANISM: Artificial Sequence
<220> FEATURE:
<223> OTHER INFORMATION: primer

<400> SEQUENCE: 63
aagatctgtc agatggatca cactgg                                         26

<210> SEQ ID NO 64
<211> LENGTH: 25
<212> TYPE: DNA
<213> ORGANISM: Artificial Sequence
<220> FEATURE:
<223> OTHER INFORMATION: primer

<400> SEQUENCE: 64
catctgacag atcttgtact gggcg                                          25

<210> SEQ ID NO 65
<211> LENGTH: 21
<212> TYPE: DNA
<213> ORGANISM: Artificial Sequence
<220> FEATURE:
<223> OTHER INFORMATION: primer

<400> SEQUENCE: 65
ttcggctgta ccaagaaggc c                                              21

<210> SEQ ID NO 66
<211> LENGTH: 24
<212> TYPE: DNA
<213> ORGANISM: Artificial Sequence
<220> FEATURE:
<223> OTHER INFORMATION: primer
```

```
<400> SEQUENCE: 66
cttggtacag ccgaaatcca gacc                                         24

<210> SEQ ID NO 67
<211> LENGTH: 24
<212> TYPE: DNA
<213> ORGANISM: Artificial Sequence
<220> FEATURE:
<223> OTHER INFORMATION: primer

<400> SEQUENCE: 67
atcggctgtc tctacgaggt cgca                                         24

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
gtagagacag ccgatgcccc                                              20

<210> SEQ ID NO 69
<211> LENGTH: 24
<212> TYPE: DNA
<213> ORGANISM: Artificial Sequence
<220> FEATURE:
<223> OTHER INFORMATION: primer

<400> SEQUENCE: 69
gatggctgta gctacgagat ctgg                                         24

<210> SEQ ID NO 70
<211> LENGTH: 23
<212> TYPE: DNA
<213> ORGANISM: Artificial Sequence
<220> FEATURE:
<223> OTHER INFORMATION: primer

<400> SEQUENCE: 70
gtagctacag ccatcgaaga cgc                                          23

<210> SEQ ID NO 71
<211> LENGTH: 24
<212> TYPE: DNA
<213> ORGANISM: Artificial Sequence
<220> FEATURE:
<223> OTHER INFORMATION: primer

<400> SEQUENCE: 71
aagggatgta ccttcaaggc tgag                                         24

<210> SEQ ID NO 72
<211> LENGTH: 23
<212> TYPE: DNA
<213> ORGANISM: Artificial Sequence
<220> FEATURE:
<223> OTHER INFORMATION: primer

<400> SEQUENCE: 72
gaaggtacat cccttaccca ggg                                          23

<210> SEQ ID NO 73
```

-continued

```
<211> LENGTH: 25
<212> TYPE: DNA
<213> ORGANISM: Artificial Sequence
<220> FEATURE:
<223> OTHER INFORMATION: primer

<400> SEQUENCE: 73
aaggcctgtg cttacgagta catcg                                          25

<210> SEQ ID NO 74
<211> LENGTH: 23
<212> TYPE: DNA
<213> ORGANISM: Artificial Sequence
<220> FEATURE:
<223> OTHER INFORMATION: primer

<400> SEQUENCE: 74
gtaagcacag gccttcttgg tgg                                            23

<210> SEQ ID NO 75
<211> LENGTH: 22
<212> TYPE: DNA
<213> ORGANISM: Artificial Sequence
<220> FEATURE:
<223> OTHER INFORMATION: primer

<400> SEQUENCE: 75
tggggctgtg gcaacctcta cg                                             22

<210> SEQ ID NO 76
<211> LENGTH: 19
<212> TYPE: DNA
<213> ORGANISM: Artificial Sequence
<220> FEATURE:
<223> OTHER INFORMATION: primer

<400> SEQUENCE: 76
gttgccacag ccccagccc                                                 19

<210> SEQ ID NO 77
<211> LENGTH: 23
<212> TYPE: DNA
<213> ORGANISM: Artificial Sequence
<220> FEATURE:
<223> OTHER INFORMATION: primer

<400> SEQUENCE: 77
cgcggttgtg atttcggctc cac                                            23

<210> SEQ ID NO 78
<211> LENGTH: 21
<212> TYPE: DNA
<213> ORGANISM: Artificial Sequence
<220> FEATURE:
<223> OTHER INFORMATION: primer

<400> SEQUENCE: 78
gaaatcacaa ccgcgtcggg c                                              21

<210> SEQ ID NO 79
<211> LENGTH: 25
<212> TYPE: DNA
<213> ORGANISM: Artificial Sequence
<220> FEATURE:
<223> OTHER INFORMATION: primer

<400> SEQUENCE: 79
```

-continued

```
ctggattgtt acaccaccaa gcagg                                            25

<210> SEQ ID NO 80
<211> LENGTH: 25
<212> TYPE: DNA
<213> ORGANISM: Artificial Sequence
<220> FEATURE:
<223> OTHER INFORMATION: primer

<400> SEQUENCE: 80
ggtgtaacaa tccagcttgg tgacg                                            25
```